(12) United States Patent
Binderup et al.

(10) Patent No.: US 8,455,466 B2
(45) Date of Patent: Jun. 4, 2013

(54) VITAMIN D ANALOGUES, COMPOSITIONS COMPRISING SAID ANALOGUES AND THEIR USE

(75) Inventors: Ernst Torndal Binderup, Taastrup (DK); Kai Holst Hansen, Herlev (DK); Claus Aage Svensgaard Bretting, Frederiksberg (DK); Martin John Calverley, Herlev (DK)

(73) Assignee: Leo Pharma A/S, Ballerup (DK)

( * ) Notice: Subject to any disclaimer, the term of this patent is extended or adjusted under 35 U.S.C. 154(b) by 1942 days.

(21) Appl. No.: 10/532,019

(22) PCT Filed: Oct. 23, 2003

(86) PCT No.: PCT/DK03/00718
§ 371 (c)(1),
(2), (4) Date: Oct. 25, 2005

(87) PCT Pub. No.: WO2004/037781
PCT Pub. Date: May 6, 2004

(65) Prior Publication Data
US 2006/0166949 A1 Jul. 27, 2006

Related U.S. Application Data

(60) Provisional application No. 60/420,783, filed on Oct. 24, 2002.

(30) Foreign Application Priority Data
Oct. 23, 2002 (DK) .................................. 2002 01608

(51) Int. Cl.
*A61K 401/00* (2006.01)
*C07C 31/59* (2006.01)

(52) U.S. Cl.
USPC ......................................... 514/167; 552/653

(58) Field of Classification Search
USPC ......................................... 514/167; 552/653
See application file for complete search history.

(56) References Cited

U.S. PATENT DOCUMENTS

| | | | | |
|---|---|---|---|---|
| 5,190,935 | A * | 3/1993 | Binderup et al. | 514/167 |
| 5,716,945 | A * | 2/1998 | Grue-Sørensen | 514/167 |
| 6,028,208 | A * | 2/2000 | Gao et al. | 552/653 |
| 6,207,656 | B1 * | 3/2001 | Carswell et al. | 514/167 |
| 6,548,489 | B2 * | 4/2003 | Takenouchi et al. | 514/167 |
| 6,867,313 | B2 * | 3/2005 | Takenouchi et al. | 552/653 |
| 6,960,573 | B2 * | 11/2005 | Takenouchi et al. | 514/167 |

FOREIGN PATENT DOCUMENTS

| | | |
|---|---|---|
| WO | WO-91/00855 | 1/1991 |
| WO | WO 92/03414 | 3/1992 |
| WO | WO-95/02577 | 1/1995 |
| WO | WO 98/58909 | 12/1998 |

OTHER PUBLICATIONS

Dorwald F. A. Side Reactions in Organic Synthesis, 2005, Wiley: VCH, Weinheim p. IX of Preface.*
Bogoslovskii, N.A.; Litvinova, G.E.; Samokhvalov, G.I.; Study of D group vitamins III, Synthesis of vitamin D3 analogs containing one or two bonds in the side chain, Zhurnal Obschchei Khimii, 1978, 48(4), pp. 908-913.
H. H. Malluche et al., Perspectives in Renal Medicine, Kidney International, vol. 62, 2002, pp. 367-374.
B. L. Onisko et al., Tetrahedron Letters, No. 13, pp. 1107-1108, 1977.
N. A. Bogoslovsky et al., Synthesis of Biologically Active Metabolites and Analogs of Vitamin D Modified in the Side Chain from Ergosterol, Vitamin D—Basic Research and its clinical Application, Proceedings of the Fourth Workshop on Vitamin D, Berlin, West Germany, Feb. 1979, A.W. Norman et at (Eds.),1979, p. 1257-1259.
L. Brandi et al., Nephrol Dial Transplant, 2002, 17, pp. 829-842.

* cited by examiner

*Primary Examiner* — Sabiha N Qazi
(74) *Attorney, Agent, or Firm* — Birch, Stewart, Kolasch & Birch, LLP

(57) ABSTRACT

Compounds according to formula I

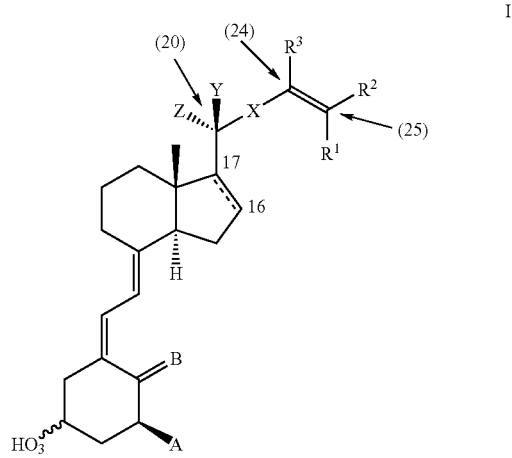

in which formula R1 and R2, which may be the same or different, represent halogen, $(C_1-C_6)$hydrocarbyl, optionally substituted with one or two hydroxyl group or one or more fluorine atoms, or, together with the carbon atom to which they are both attached, R1 and R2 form a $(C_3-C_6)$carbocyclic ring, or one of R1 and R2 taken together with R3 forms a direct bond, such that a triple bond is constituted, or R1 and R2 represent both hydrogen; R3 when not forming a direct bond with one of R1 and R2 represents hydrogen or $(C_1-C_3)$ hydrocarbyl; X represents (E)-ethylene, (Z)-ethylene, ethynylene, or a bond; Y and Z independently represent hydrogen or methyl; and prodrugs and stereo isomeric forms thereof are provided together with their use in therapy, and their use in the manufacture of medicaments.

11 Claims, No Drawings

VITAMIN D ANALOGUES, COMPOSITIONS COMPRISING SAID ANALOGUES AND THEIR USE

This National Phase PCT application claims priority under 35 U.S.C. 119(e) on U.S. Provisional Application No(s). 60/420,783 filed on Oct. 24, 2002 and under 35 U.S.C. 119(a) on Patent Application No(s). PA 2002 01608 filed in Japan on Oct. 23, 2002, all of which which are hereby incorporated by reference.

FIELD OF INVENTION

This invention relates to novel vitamin D analogues, to their use in therapy, to pharmaceutical compositions comprising said analogues, to methods of treatment comprising the administration of said analogues to patients in need thereof, and to the use of said analogues in the manufacture of medicaments.

BACKGROUND OF THE INVENTION

Over the last decades there has been a growing understanding of the biological effects of vitamin D. The classical actions of vitamin D involve calcium and phosphate absorption from the intestines, which is vital to the mineral balance and to the build-up and maintenance of bones. Another primary action of vitamin D is the regulation of the excretion of the parathyroid hormone (PTH) from the parathyroid glands. Vitamin D inhibits the production of the parathyroid hormone, so that a low level of vitamin D in the blood will lead to a high level parathyroid hormone, and vice versa. Vitamin D exerts its effect through an intriguing mechanism whereby the production of the mRNA which is translated into the parathyroid hormone, or a proform thereof, is inhibited. The impact of vitamin D in biological systems, however, reaches beyond these effects. Vitamin D appears to have profound effects on muscles, the immune system, the reproductive system, and cell proliferation and differentiation. Cells holding the vitamin D receptor (VDR) have, in fact, been found in many parts of the body, including the intestines, kidneys, prostate, bone, bone marrow, parathyroid glands, skin, liver, muscle and lymphoid tissue. The widespread existence of VDR have made vitamin D and analogues thereof attractive compounds for the treatment of various diseases including cancer, skin and bone diseases and autoimmune diseases.

The invention relates to a novel class of vitamin D analogues that show a potent suppressive effect on the secretion of parathyroid hormone, i.e. which can be used in the treatment of secondary hyperparathyroidism (s-HPT). A crucial structural element in active vitamin D are the two hydroxyl groups in positions 1 and 25. In contrast to that, the compounds of the present invention are characterized by a blocking of the 25-position, so that they do not have hydroxyl groups in that position, nor can they be hydroxylated in that position in vivo by a P450-like enzyme.

Vitamin D analogues with some structural resemblance to the compounds of the present invention have previously been disclosed. As an example, WO95/02577 teaches compounds of the formula

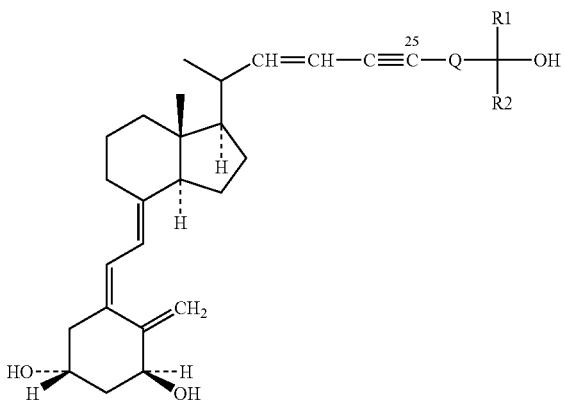

WO91/00855 discloses compounds of the formula

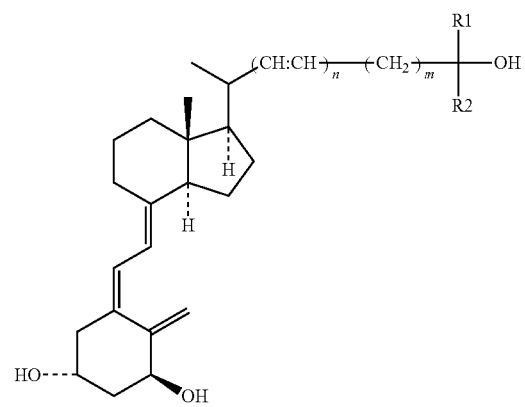

and Onisko, *Tetrahedron Lett.*, 1107-1108, 13, 1977 discloses a compound of the formula

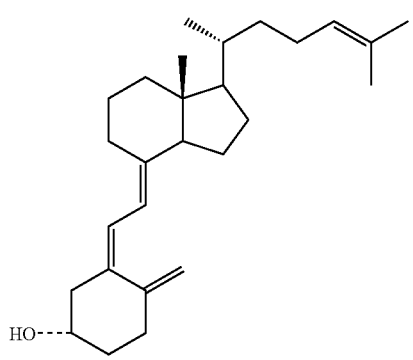 [SMILES: C=C1CC[C@H](O)C/C1=C/C=C1\CCC[C@@]2(C)C1CCC2[C@H](C)CCC=C(C)C]

which is useful for inhibition of liver enzymes responsible for hydroxylation of vitamin $D_3$ to 25-OH vitamin $D_3$.

Finally, Bogoslovsky et al, *Vitamin D—Basic Research and its Clinical Application, proceedings of the Fourth Workshop on Vitamin D*, Berlin West Germany 1979, A. W. Norman et al (Eds.), p 1257-1259, Walter de Gruyter, Berlin 1979, discloses a synthetic study including the preparation of 3(S)-hydroxy-9,10-secocholesta-5(Z),7(E),10(19),22(E), 24-penta-ene. This reference, however, does not disclose any biological data on this particular compound.

Vitamin D and analogues thereof are already used in the treatment of s-HPT. Paricalcitol (19-nor-1,25-dihydroxy-vitamin $D_2$) and doxercalciferol (1α-hydroxy-vitamin $D_2$) are approved in the USA for treatment of s-HPT, and 22-oxa-calcitriol (maxacalcitol) and hexafluoro-calcitriol (falecalcitriol) are approved in Japan [Malluche, *Kidney Int.*, 367-374, 62, 2002]. Moreover, calcitriol itself and a prodrug thereof 1α(OH)$D_3$ are also used in the treatment and prophylaxis of s-HPT [Brandi, *Nephrol Dial Transplant*, 829-842, 17, 2002].

All therapeutic interventions which include administration of vitamin D and analogues thereof must pay attention to the adverse side effects often associated with this kind of therapy, in particular the calcemic effects of vitamin D compounds. These side effects may severely restrict or even prevent the use of such compounds, in spite of other clinically positive effects. The present invention therefore seeks to provide vitamin D analogues which have a reduced calcemic effect while retaining a suppressive effect on the secretion of the parathyroid hormone.

SUMMARY OF THE INVENTION

Accordingly, the present invention provides compounds represented by formula I

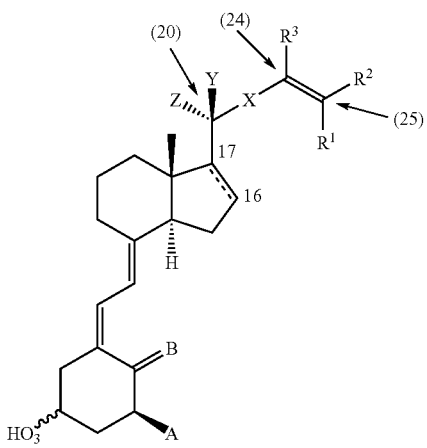

in which formula

R1 and R2, which may be the same or different, represent halogen, ($C_1$-$C_6$)hydrocarbyl, optionally substituted with one or two hydroxyl group or one or more fluorine atoms, or, together with the carbon atom to which they are both attached, R1 and R2 form a ($C_3$-$C_6$)carbocyclic ring, or one of R1 and R2 taken together with R3 forms a direct bond, such that a triple bond is constituted, or R1 and R2 both represent hydrogen;

R3 when not forming a direct bond with one of R1 and R2 represents hydrogen or ($C_1$-$C_3$)hydrocarbyl;

X represents (E)-ethylene, (Z)-ethylene, ethynylene, or a bond;

Y and Z independently represent hydrogen or methyl; the bond between C#16 and C#17 is depicted with a dotted line to illustrate that said bond may be either a single bond, in which case the projection of the ring substituent is beta, or a double bond;

A represents hydroxyl, fluorine or hydrogen;

B represents $CH_2$ or $H_2$;

the configuration in the 3-position corresponds to the same configuration as in natural vitamin $D_3$ (normal), or the configuration in the 3-position is opposite to natural vitamin $D_3$ (epi);

with the proviso that when X represents (E)-ethylene or (Z)-ethylene, one of R1 and R2 taken together with R3 may not form a direct bond, such that a triple bond is constituted;

with the further proviso that when X represents a bond R1 and R2 are not hydrogen;

with the further proviso that the compound of formula I is not 3(S)-hydroxy-9,10-secocholesta-5(Z),7(E),10(19),22(E),24-penta-ene;

and prodrugs and stereo isomeric forms thereof.

In the compounds according to formula I, the blocking of the 25-position is achieved by the presence of a carbon-carbon double- or triple bond between carbon #24 and #25. In this way, the 25-position cannot be hydroxylated. As discussed more thoroughly later, recent data suggest that hydroxylation in the 25-position has limited consequences for the parathyroid hormone suppressing effect. Vitamin D analogues which are blocked for hydroxylation in the 25-position therefore retain their parathyroid hormone suppressing effect while being deprived other vitamin D activities, e.g. the calcemic effect, associated with an intact vitamin D structure.

In another aspect, the invention relates to the use of a compound according to formula I in therapy.

In another aspect, the invention relates to a pharmaceutical composition comprising a compound according to formula I.

In still another aspect, the invention relates to methods of treatment comprising the step of administering compounds according to formula I to a patient in need thereof.

In a still further aspect, the invention relates to the use of a compound according to formula I in the manufacture of a medicament.

DETAILED DESCRIPTION OF THE INVENTION

In a preferred embodiment of the invention, R1 and R2 when taken separately, independently represent bromo, chloro, methyl, ethyl, trifluoromethyl, hydroxymethyl, (1- or 2-)hydroxyethyl, normal, iso- or cyclopropyl, 2-hydroxy-9-propyl, 2-methyl-2-propyl, 3-pentyl or 3-hydroxy-3-pentyl.

In another preferred embodiment, R1 and R2 are the same, and both represent hydrogen, methyl, ethyl, bromo, chloro, or trifluoromethyl.

In another embodiment R1 and R2 when taken together with the carbon atom to which they are both attached to form a $C_3$ carbocyclic ring, a $C_4$ carbocyclic ring, a $C_5$ carbocyclic ring, or a $C_6$ carbocyclic ring.

In another preferred embodiment, R1 and R2 when taken together include ethylene, tri-methylene, tetra-methylene, or penta-methylene, such as R1 and R2 when taken together with the carbon atom to which they are both attached to form a $C_3$ carbocyclic ring, a $C_4$ carbocyclic ring, a $C_5$ carbocyclic ring, or a $C_6$ carbocyclic ring.

In another preferred embodiment, when R2 constitutes part of a triple bond, then R1 represents a branched $C_{1-6}$ hydrocarbyl, optionally substituted with one or two hydroxyl groups. In particular, R1 represents a branched $C_{1-6}$ hydrocarbyl, optionally substituted with one hydroxyl group, such as —$CMe_3$, —$C(OH)Me_2$ or —$C(OH)Et_2$.

In another preferred embodiment, R3, when not part of a triple bond, represents hydrogen, methyl or cyclopropyl.

In another preferred embodiment A is hydroxyl or fluoro.

In another preferred embodiment R1 and R2 are a radical obtained by removal of one hydrogen atom from a straight, branched, or cyclic saturated $C_{1-6}$ hydrocarbon.

In particular, compounds of formula I may be selected from amongst the list consisting of 1(S),3(R)-Dihydroxy-9,10-secocholesta-5(Z),7(E),10(19),22(E),24-penta-ene (Compound 1), 1(S),3(R)-Dihydroxy-9,10-secocholesta-5(Z),7(E),10(19), 22(Z),24-penta-ene (Compound 2),
20(S),1(S),3(R)-Dihydroxy-9,10-secocholesta-5(Z),7(E),10 (19),22(E),24-penta-ene (Compound 3),
1(S),3(R)-Dihydroxy-9,10-seco-26,27-cyclo-cholesta-5(Z), 7(E),10(19),22(E),24-penta-ene (Compound 4),
20(S),1(S),3(R)-Dihydroxy-9,10-seco-26,27-cyclo-cholesta-5(Z),7(E),10(19),22(E),24-penta-ene (Compound 5),
1(S),3(R)-Dihydroxy-9,10-seco-26,27-methano-cholesta-5 (Z),7(E),10(19),22(E),24-penta-ene (Compound 6),
20(S),1(S),3(R)-Dihydroxy-9,10-seco-26,27-methano-cholesta-5(Z),7(E),10(19),22(E),24-penta-ene (Compound 7),
1(S),3(R)-Dihydroxy-20(S)-(4,4-dibromo-1,3-butadien-1yl)-9,10-seco-pregna-5(Z),7(E),10(19)-triene (Compound 8),
1(S),3(R),26-Trihydroxy-9,10-secocholesta-5(Z),7(E),10 (19),22(E),24(E)-penta-ene (Compound 9),
20(S),1(S),3(R),26-Trihydroxy-9,10-secocholesta-5(Z),7 (E),10(19),22(E),24(E)-penta-ene (Compound 10),
1(S),3(R),26-Trihydroxy-9,10-secocholesta-5(Z),7(E),10 (19),22(E),24(Z)-penta-ene (Compound 11),
20(S),1(S),3(R),26-Trihydroxy-9,10-secocholesta-5(Z),7 (E),10(19),22(E),24(Z)-penta-ene (Compound 12),
1(S),3(R)-Dihydroxy-20(R)-(4-methyl-5-ethyl-5-hydroxy-1 (E),3(E)-heptadienyl)-9,10-secopregna-5(Z),7(E),10(19)-triene (Compound 13),
1(S),3(R)-Dihydroxy-20(R)-(3-cyclopropyl-1(E),3-butadienyl)-9,10-secopregna-5(Z),7(E),10(19)-triene (Compound 14),
1(S),3(R)-Dihydroxy-9,10-secocholesta-5(Z),7(E),10(19), 24-tetra-ene-22-yne (Compound 15),
1(S),3(R)-Dihydroxy-20(R)-(5-methyl-5-hydroxy-1,3-hexadiynyl)-9,10-secopregna-5(Z),7(E),10(19)-triene (Compound 16),
1(S),3(R)-Dihydroxy-20(S)-(5-ethyl-5-hydroxy-1,3-heptadiynyl)-9,10-secopregna-5(Z),7(E),10(19)-triene (Compound 17),
1(S),3(R)-Dihydroxy-20(R)-(5-ethyl-5-hydroxy-1,3-heptadiynyl)-9,10-secopregna-5(Z),7(E),10(19)-triene (Compound 18),
1(S),3(R)-Dihydroxy-20(R)-(5,5-dimethyl-1,3-hexadiynyl)-9,10-secopregna-5(Z),7(E),10(19)-triene (Compound 19),
1(S),3(R)-Dihydroxy-20(S)-(5,5-dimethyl-1,3-hexadiynyl)-9,10-secopregna-5(Z),7(E),10(19)-triene (Compound 20),
1(S)-Fluoro-3(R)-hydroxy-9,10-secocholesta-5(Z),7(E),10 (19),22(E),24-penta-ene (Compound 21),
1(S),3(R)-Dihydroxy-19-nor-9,10-secocholesta-5,7(E),22 (E),24-tetra-ene (Compound 22),
1(S),3(S)-Dihydroxy-9,10-secocholesta-5(Z),7(E),10(19), 22(E),24-penta-ene (Compound 23),
1(S),3(R)-Dihydroxy-9,10-secocholesta-5(Z),7(E),10(19), 16,22(E),24-hexa-ene (Compound 24),
1(S),3(R)-Dihydroxy-26,26,26,27,27,27-hexafluoro-9,10-secocholesta-5(Z),7(E),10(19),22(E),24-penta-ene (Compound 25),
3(S),26-Dihydroxy-9,10-secocholesta-5(Z),7(E),10(19),22 (E),24(E)-penta-ene (Compound 26),
1(S),3(R)-Dihydroxy-20(R)-(4,4-dibromo-1,3-butadien-1-yl)-9,10-seco-pregna-5(Z),7(E),10(19)-triene (Compound 27),
1(S),3(R)-Dihydroxy-26,27-dimethyl-9,10-secocholesta-5 (Z),7(E),10(19),22(E),24-penta-ene (Compound 28),
1(S),3(S)-Dihydroxy-26,27-dimethyl-9,10-secocholesta-5 (Z),7(E),10(19),22(E),24-penta-ene (Compound 29),
1(S),3(R)-Dihydroxy-24-methyl-26,27-methano-9,10-secocholesta-5(Z),7(E),10(19),22(E),24-penta-ene (Compound 30),
1(S),3(R)-Dihydroxy-20(R)-(4,4-dichloro-1,3-butadien-1-yl)-9,10-seco-pregna-5(Z),7(E),10(19)-triene (Compound 31),
1(S),3(R)-Dihydroxy-26,27-ethano-9,10-secocholesta-5(Z), 7(E),10(19),22(E),24-penta-ene (Compound 32),
1(S),3(R)-Dihydroxy-26,27-propano-9,10-secocholesta-5 (Z),7(E),10(19),22(E),24-penta-ene (Compound 33),
1(S),3(R)-Dihydroxy-20(S)-cyclopropylidenemethyl-9,10-seco-pregna-5(Z),7(E),10(19)-triene (Compound 34),
1(S),3(R)-Dihydroxy-20(R)-cyclopropylidenemethyl-9,10-seco-pregna-5(Z),7(E),10(19)-triene (Compound 35),
20(S),1(S),3(R)-Dihydroxy-26,26,26,27,27,27-hexafluoro-9,10-secocholesta-5(Z),7(E),10(19),22(E),24-penta-ene (Compound 36).

Compounds of formula I may comprise chiral centres, such as asymmetrically substituted carbon atoms, and carbon-carbon double bonds which give rise to the existence of stereo isomeric forms, such as enantiomers, diastereomers, and geometric isomers (cis/trans). The present invention relates to all such forms, either in pure form or as mixtures thereof.

For example the configuration at C-3 or at C-20 (when Y is different from Z) of formula I can be R or S, or when X is ethylene the configuration can be E or Z.

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

In the present context, unless stated differently, the term "prodrug" is intended to indicate compounds in which one or more hydroxyl groups are masked as groups which can be reconverted to hydroxyl groups in vivo so as to provide compounds of formula I upon administration to a patient. Examples of said groups are esters, e.g carboxylic acid esters and phosphate acid esters. It is well-known that proforms of vitamin D are hydroxylated in the liver and kidneys to reach the biologically active state. In line with this, compounds of formula I in which A is hydroxyl are preferred ones, but compounds in which A is hydrogen are, in fact, another type of prodrug, which may be hydroxylated into an active state upon administration to a patient.

In the present context, the term "hydrocarbyl" is intended to indicate the radical obtained by removal of one hydrogen atom from a straight, branched, and/or cyclic, saturated or unsaturated hydrocarbon. Said straight, branched, and/or cyclic, saturated or unsaturated hydrocarbon include but are not limited to methyl, ethyl, 1-propyl, 2-propyl, 1-butyl, 2-butyl, 1-pentyl, 2-pentyl, 3-pentyl, 1-hexyl, 2-hexyl, 3-hexyl, cyclopropyl, cyclobutyl, cyclopentyl, cyclohexyl, 2-methyl-2-propyl, 2-methylcyclopropyl, 2-methylallyl, 1-prop-2-ynyl, 1-but-2-ynyl, 3-methyl-1-pentyl, 1-hex-1-en-3-ynyl.

In the present context the term "halogen" is intended to indicate compounds from the seventh main group in the periodic table, i.e. fluoro, chloro, bromo and iodo, and in particular chloro and bromo.

The terms "normal" and "epi" when used to describe the absolute configuration of a compound of the present invention relates to the absolute configuration of the natural vitamin $D_3$ itself. Hence, if the configuration at a given carbon is referred to as "normal", it corresponds to the configuration of vitamin $D_3$ on that particular carbon atom. Likewise, if the configuration at a given carbon is referred to as "epi", it is the opposite configuration to that of vitamin D on that particular carbon atom.

Of particular relevance for the present invention is the treatment of secondary hyperparathyrodism (s-HPT), e.g. in connection with renal failure, using vitamin D and its analogues. Hyperparathyrodism is a disease characterised by increased secretion of the parathyroid hormone from the parathyroid glands. In s-HPT, the cause for the elevated excretion is not malfunctioning of the glands, but rather factors outside the glands, e.g. failing kidneys. Vitamin D is absorbed from the food or produced in the skin in a proform which has to be activated to reach its biologically active state. Part of this activation takes place in the kidneys as a hydroxylation of the proform. In patients with failing kidneys, e.g. dialysis patients, this hydroxylation is impaired, resulting in a lower level of active vitamin D in the blood. As mentioned above, a low level of vitamin D leads to a high production of the parathyroid hormone, and this pathological condition is termed secondary hyperparathyroidism.

The parathyroid hormone has a powerful influence on the cells in the bones causing them to release calcium into the blood stream. Under non-pathological conditions this process is well-balanced to secure an adequate calcium level in the bones. However, at elevated parathyroid hormone levels for extended periods of time, the bones will lose too much calcium and will become brittle and thus more prone to fracture. This condition is referred to as osteodystrophy and osteomalacia from which renal patients are often suffering. Prolonged exposure to parathyroid hormones is also found to have toxic effects on many vital organs, e.g. the heart, skeletal muscles, the nerves and the reproductive system [Malluche, *Kidney Int.*, 367-374, 62, 2002].

One way of controlling the level of parathyroid hormone is to administer vitamin D or analogues thereof which will inhibit the secretion of said hormone. Such therapeutic intervention, however, may be hampered by serious adverse side effects often associated with vitamin D therapy. As mentioned previously, an effect of vitamin D and many analogues thereof is an increased uptake of calcium from the intestine which may lead to hypercalcemia. This effect may restrict the utility of vitamin D analogues, which in other respects are beneficial. The aim for much of the on-going vitamin D research is thus to minimize the calcemic effect while maximizing the clinical effect. Ideally, if the structural moieties in the vitamin D molecule responsible for the different activities of vitamin D were identified, it would be possible to manipulate these structures to obtain selectivity, e.g. no calcemic activity but high parathyroid hormone secretion suppressive effect. Unfortunately, no such clear structure-activity relation has been established yet. However, a recent observation by Brandi in *Nephrol Dial Transplant*, 829-842, 17, 2002 might be helpful in this respect. Brandi compares the PTH suppressive effect of calcitriol, i.e. $1,25(OH)_2 D_3$ and its proform, $1\alpha(OH)D_3$. $1\alpha(OH)D_3$ is hydroxylated in the liver to $1,25(OH)_2D_3$, and due to the different pharmacokinetics of the two compounds, the bioavailability of $1,25(OH)_2D_3$ was markedly lower when $1\alpha(OH)D_3$ was administered to the patient than when $1,25(OH)_2 D_3$ was administered. In spite of this difference in the availability of $1,25(OH)_2 D_3$ in the two dosing regimes, there was no significant difference in the suppression of the secretion of PTH. This leads to the speculation that the 25-hydroxyl group is not mandatory for the PTH suppressive effect. One way of achieving the desired selectivity could thus be to block the 25-position in the vitamin D structure so that it cannot be hydroxylated, and in this way maintaining or even increasing the PTH suppressive effect while dispossessing the molecule of other vitamin D related activities, and in particular its calcemic effect.

The calcemic activities of the compounds of the present invention were determined in rats in vivo, as previously described (Binderup, L., Bramm, E., Biochem. Pharmacol. 37, 889-895 (1988)). The PTH suppressive effect of the compounds of the present invention was tested in vitro on bovine parathyroidea cells: Fresh bovine parathyroid glands were collected from adult cattle within 20 min of slaughter. From minced parathyroid tissue dispersed parathyroid cells were prepared as previously described (E. M. Brown, S. Hurwitz and G. D Aurbach; Preparation of viable isolated bovine parathyroid cells; Endocrinology, 1976, vol 99, no 6, 1582-1588). Then, the cells were treated with vitamin D analogues for 60 hours at 37° C. and the PTH secretion was determined.

Table A lists these PTH suppressive effects and the calcemic activities of compounds of the present invention. Calcitriol ($1,25(OH)_2D_3$) is used as a reference compound.

TABLE A

In vivo calcemic activity in rats according to Binderup et al. Biochem. Pharmacol. 37, 889-895 (1988) and the PTH suppressive effect tested in vitro on bovine parathyroidea cells according to the protocol above of compounds of the present invention relative to Calcitriol ($1,25(OH)_2D_3$).

| Compound | In vivo calcemic activity relative to Calcitriol ($1,25(OH)_2D_3$) | In vitro PTH secretion relative to untreated bovine parathyroidea cells (untreated cells as control = 100%) |
|---|---|---|
| Calcitriol | 100% | 60% |
| 1 | <10% | 57% |
| 3 | 1% | 61% |
| 6 | 1% | 56% |
| 7 | <0.5% | 65% |
| 25 | 8% | 74% |
| 27 | <0.5% | 65% |
| 28 | 1% | 62% |

The data listed in Table A show that the compounds of the present invention have a comparable PTH suppressive effect as the reference compound Calcitriol ($1,25(OH)_2D_3$), together with a surprisingly lower calcemic effect than the reference compound.

The compounds of the present invention thus surprisingly show a high selectivity for e.g. the inhibition of the production of the parathytoidea hormone without the unwanted effects of vitamin D analogues, such as $1,25(OH)_2D_3$, on the calcium balance in the organism, including calcemic and calciuric activities.

In a particular embodiment, the invention thus provides a method for treating, preventing or ameliorating s-HPT, and in particular s-HPT associated with renal failure, the method comprising administering to a patient in need thereof an effective amount of a compound of formula I. Optionally, said method may include treatment with other therapeutically active compounds normally used in the treatment of the above mentioned disease. Said compounds may be administered concomitantly or sequentially with compounds of the present invention, and in they particular include phosphate binders.

The use of compounds of the present invention may not be limited to the treatment of s-HPT. It is well-known that vitamin D and analogues thereof may be beneficial in the treatment of a variety of diseases due to a strong activity in inducing differentiation and inhibiting undesirable proliferation of certain cells, including skin cells and cancer cells, as well as an immunomodulating effect and an effect in bone build-up and maintenance (Brown A J: Vitamin D analogues. Am J Kidney Dis 32 (Suppl): S25-S39, 1998; Brown A J et al.: Vitamin D. Am Physiol 277:F157-F175, 1999). Accordingly, the invention also provides a method of treating, preventing or ameliorating diseases characterised by abnormal cell differentiation and/or cell proliferation, cancer, leukemia, mammary cancer, brain glial cancer, osteosarcoma, melanoma, myelofibrosis, psoriasis, primary hyperparathyroidism, diabetes melitus, discoid and systemic lupus erythematosus, chronic dermatoses of autoimmune type, hypertension, acne, alopecia, skin aging, AIDS, neurodegenerative disorders, Alzheimer's disease, host versus graft and graft versus host reactions, rejections of transplants, steroid induced skin atrophy and osteroporosis, and for inducing osteogenesis, the method comprising administering to a patient in need thereof an effective amount of a compound of formula I. Optionally, said method may include treatment with other therapeutically active compounds normally used in the treatment of the above mentioned diseases. Said compounds may be administered concomitantly or sequentially with compounds of the present invention, and they include phosphate binders, steroids and anti-proliferative agents.

In the systemic treatment using the present invention daily doses of from 0.001-2 µg per kilogram body weight, preferably from 0.002-0.3 µg/kg of mammal body weight, for example 0.003-0.3 µg/kg of a compound of formula I is administered, typically corresponding to a daily dose for an adult human of from 0.1 to 200 µg. A suitable dosing regime may, however, also include dosing with longer intervals, e.g. every other day, every week, or even with longer intervals. In the topical treatment of dermatological disorders, ointments, creams or lotions containing from 0.1-1000 µg/g, and preferably from 0.1-500 µg/g, for example 0.1-200 µg/g of a compound of formula I is administered. For topical use in ophthalmology ointments, drops or gels containing from 0.1-1000 µg/g, and preferably from 0.1-500 µg/g, for example 0.1-100 µg/g of a compound of formula I is administered. The oral compositions are formulated, preferably as tablets, capsules, or drops, containing from 0.07-100 µg, preferably from 0.1-50 µg, of a compound of formula I per dosage unit.

In a further preferred aspect, the invention relates to a pharmaceutical composition comprising a compound of formula I. The formulations of the present invention, both for veterinary and for human medical use, comprise active ingredients in association with a pharmaceutically acceptable carrier(s) and optionally other therapeutic ingredient(s). The carrier(s) must be "acceptable" in the sense of being compatible with the other ingredients of the formulations and not deleterious to the recipient thereof.

Conveniently, dosage unit of a formulation contain between 0.05 µg and 100 µg, preferably between 0.1 µg and 50 µg of a compound of formula I.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers.

The formulations include e.g. those in a form suitable for oral (including sustained or timed release), rectal, parenteral (including subcutaneous, intraperitoneal, intramuscular, intraarticular and intravenous), transdermal, ophthalmic, topical, nasal or buccal administration.

The formulations may conveniently be presented in dosage unit form and may be pre-pared by any of the methods well known in the art of pharmacy, e.g as disclosed in Remington, *The Science and Practice of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like Or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for nasal or buccal administration include powder, self-propelling and spray formulations, such as aerosols and atomisers.

Prodrugs of the present invention may also be delivered by use of monoclonale antibodies as individual carriers to which the compound molecules are coupled.

In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

Furthermore, said formulations may also comprise other therapeutically active compounds normally used in the treatment of the above mentioned diseases. Examples of such compounds include phosphate binders, steroids and anti-proliferative agents.

In still another aspect, the invention relates to the use of a compound of formula I, optionally together with another therapeutically active compound in the manufacture of a medicament intended for the treatment of abnormal cell differentiation and/or cell proliferation, cancer, leukemia, mammary cancer, brain glial cancer, osteosarcoma, melanoma, myelofibrosis, psoriasis, primary hyperparathyroidism, s-HPT, s-HPT in association with renal failure, diabetes melitus, discoid and systemic lupus erythematosus, chronic dermatoses of autoimmune type, hypertension, acne, alopecia, skin aging, AIDS, neurodegenerative disorders, Alzheimer's disease, host versus graft and graft versus host reactions, rejections of transplants, steroid induced skin atrophy and osteroporosis, and for inducing osteogenesis. Said other therapeutically active compound may conveniently be selected from amongst, e.g. phosphate binders, steroids and anti-proliferative agents.

A compound of formula I may be prepared from the intermediates 1 according to the reaction Scheme 1.

Scheme 1

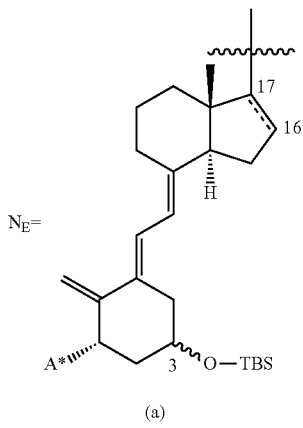

(a)

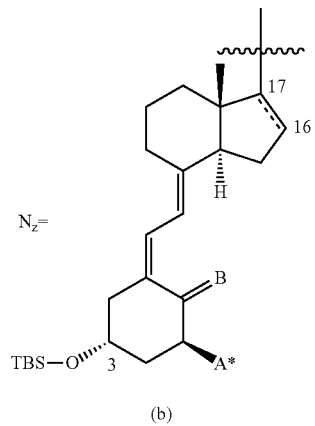

(b)

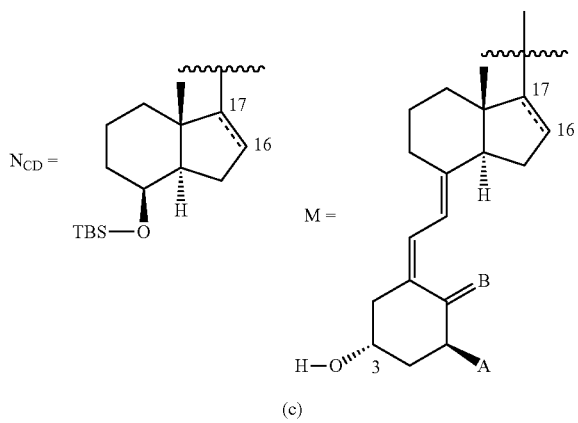

(c)

-continued

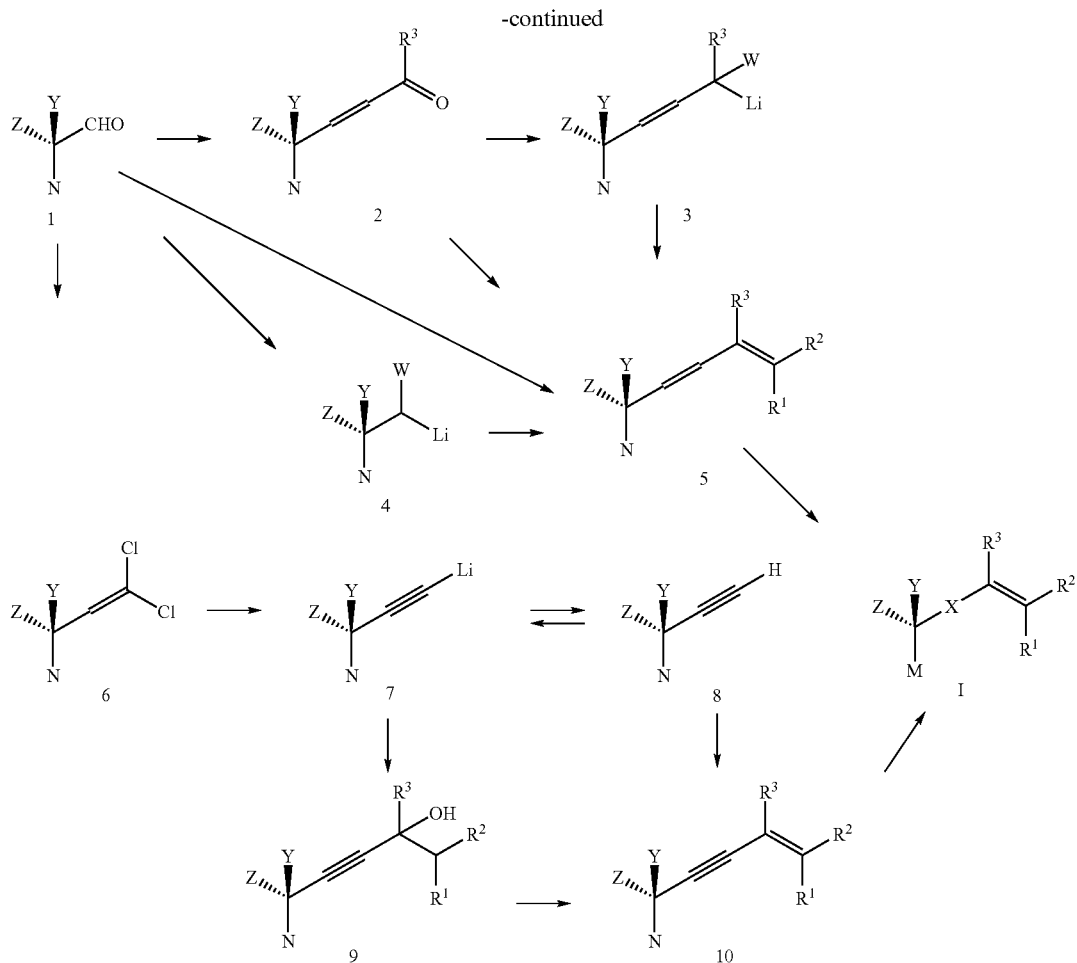

The symbol * is used in this Scheme to indicate that the group A* in an intermediate compound may either be identical to the group A as found in compound I (for example, fluorine in $N_Z$), or alternatively may be a group that can be converted to this at any subsequent stage in the synthesis (for example, silyl ether protected hydroxyl in $N_Z$). Although not formally indicated in this manner, the same situation may also apply for the variables $R^1$, $R^2$, $R^3$, Y, and Z on Scheme 1. Furthermore, the identity of N (i.e. $N_E$, $N_Z$, or $N_{CD}$) and/or of one or more variable group(s) may change from intermediate to intermediate along the reaction sequence. However the actual identity will be apparent from the particular context. Note that while Cl and Li are atomic symbols (as are C, H, and O), the letter W is used as an abbreviation for a functional group or element that stabilises the organo-lithium species. The configuration (E or Z) of the double bond (to become X=ethylene in the final compounds I) is left unspecified in Scheme 1 (by drawing a linear arrangement) but is specified as and when required.

Starting materials of type 1 and certain examples of intermediates of type 2, 4, 6, 7, and 8 are well known to a person skilled in the art and have been described in the literature such as by G.-D. Zhu and W. H. Okamura in Chem. Rev. 1995, 95, 1877-1952. The suffixes, a, b and c, identify the structure of the N group, as defined at the top of Scheme 1.

In outline, the suggested reactions, all well known to the synthetic organic chemist skilled in the art of vitamin D chemistry, are carried out as follows. Standard abbreviations are used throughout this disclosure, e.g. Ac=acetyl; aq.=aqueous; DCM=dichloromethane; Et=ethyl; ether=diethylether; h=hour(s); LDA=lithium diisopropylamide; Me=methyl; PDC=pyridinium dichromate; TBA=tetra (n)butylammonium; TBS=t-butyldimethylsilyl; TMS=trimethylsilyl; Ts=p-tosyl; DIBAL=diisobutylaluminium hydride; Ph=phenyl; THF=tetrahydrofuran; v=volume.

1→2 Wittig or Wadsworth-Emmons reaction [e.g. Wittig with $Ph_3P=CH—C(O)R^3$ (for R3=H, via the R3=OMe intermediate, from which it is derived by sequential DIBAL reduction and PDC or Dess-Martin periodinane oxidation).] The configuration of the double bond established in this reaction is usually E (small amounts of the Z intermediate can often be isolated however), but conditions can be selected to give an increased proportion of the Z intermediate, e.g. a modification of the Wadsworth-Emmons reaction using $(CF_3CH_2O)_2P(O)—CH_2C(O)OMe$. The E-configuration can alternatively be converted to Z by photoisomerisation at the stage of intermediate 2. Separation of the required isomer from a mixture of E and Z isomers can be performed at this or a later convenient stage by e.g. chromatography or crystallisation.

1→4 For intermediates with $W=S(O_2)Ph$ or W=SeMe, methods have been described in the literature, such as by M. J. Calverly, Tedrahedron Letters 1987, 28, 1337-1340.

1→5 E.g. by Wittig reaction with $Ph_3P=CH—C(R^3)=CR^1R^2$. E and Z isomers formed in this reaction can optionally be separated by e.g. chromatography or crystallisation at this stage or any later stage in the synthesis.

1→6→7→8→7 The dibromo-intermediate may be used instead of the shown dichloro-intermediate (6) in this part of a well-known reaction sequence for making alkynes as described earlier by e.g. W. G. Salmond et al., Tetrahedron Letters 1977, 14, 1239-1240.

2→3 For $R^3$=H (in 3): Sequential DIBAL reduction [for $R^3$=OMe (or H) in 2 (see 1→2), conversion of the alcohol to a leaving group (e.g. Cl or OTs) which is then substituted to incorporate W (e.g. —P(O)Ph2 or —S($O_2$)Ph, either directly or via oxidation of the lower oxidation state —PPh2 or —SPh, all available as salts), and lithiation (e.g. with n-BuLi or LDA).

2→5 Wittig reaction e.g. with $Ph_3P$=$CR^1R^2$ or Wadsworth-Emmons reaction e.g. using $(EtO)_2P(O)$—$CR^1R^2$. The separation of 24-E and 24-Z isomers formed in this reaction can can optionally be separated by e.g. chromatography or crystallisation at this stage or any later stage in the synthesis.

3→5 Coupling reaction with a carbonyl compound, e.g. by a Horner reaction when W=P(O)Ph2, or by a Julia reaction when W=S($O_2$)Ph (followed in the latter reaction by a reductive elimination of W together with the oxy-group). The separation of 24-E and 24-Z isomers formed can optionally be separated by e.g. chromatography or crystallisation at this stage or any later stage in the synthesis.

4→5 Coupling reaction with a carbonyl compound followed by elimination of W and the oxy-group. Separation of the required isomer from a mixture of E and Z isomers can be performed at this or a later convenient stage.

7→9 Coupling reaction with a carbonyl compound.

8→10 Palladium catalysed cross coupling with a terminal acetylene or with a vinyl or acetylenic derivative such as a halogenide (e.g. bromide). The reactions include, but are not limited, to Heck, Suzuki, Cadiot-Chodkiewski; Negishi, Sonogashira, and Stille type reactions.

9→10 Dehydration with Martin's sulfurane reagent.

5 or 10→I "N→M": see below. In addition A*, $R^1$, $R^2$, $R^3$, Y, and/or Z may be transformed or derivatised by methods and general procedures well known to a person skilled in the art, such as described in "Comprehensive Organic Transformations", by R. C. Larock, VCH 1989.

$N_{CD}$→M: Sequential desilylation with HF to give the alcohol, oxidation with Dess-Martin periodinane to the ketone, and Horner-Wittig coupling with the lithio-derivative of the requisite known A-ring phosphine oxide of formula II to give $N_Z$. Then desilylation with HF or TBA-fluoride.

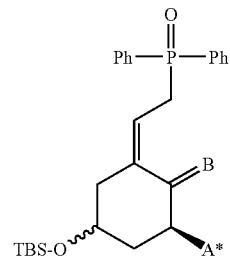

II $N_E$→M: Conversion to $N_Z$ (B=$CH_2$) by triplet-sensitised photoisomerisation, then desilylation with HF or TBA-fluoride.

$N_Z$→M: Desilylation with HF or TBA-fluoride.

The invention is further illustrated by the following Preparations and Examples: The exemplified compounds according to formula I are listed in Table 1, whereas the starting materials and intermediates of general formulae 1 through 10 (Scheme 1) are listed in Table 2.

TABLE 1

| Compound | Example Number | General Procedure | A | B | 3-Configuration | 16,17-bond | X | Y | Z | R1 | R2 | R3 |
|---|---|---|---|---|---|---|---|---|---|---|---|---|
| 1 | 1 | 9 | OH | $CH_2$ | normal | single | E-ethylene | H | Me | Me | Me | H |
| 2 | 2 | 9 | OH | $CH_2$ | normal | single | Z-ethylene | H | Me | Me | Me | H |
| 3 | 3 | 9 | OH | $CH_2$ | normal | single | E-ethylene | Me | H | Me | Me | H |
| 4 | 4 | 8 | OH | $CH_2$ | normal | single | E-ethylene | H | Me | —$(CH_2)_2$— | | H |
| 5 | 5 | 9 | OH | $CH_2$ | normal | single | E-ethylene | Me | H | —$(CH_2)_2$— | | H |
| 6 | 6 | 9 | OH | $CH_2$ | normal | single | E-ethylene | H | Me | —$(CH_2)_3$— | | H |
| 7 | 7 | 9 | OH | $CH_2$ | normal | single | E-ethylene | Me | H | —$(CH_2)_3$— | | H |
| 8 | 18 | 8 | OH | $CH_2$ | normal | single | E-ethylene | Me | H | Br | Br | H |
| 9 | 8 | 9 | OH | $CH_2$ | normal | single | E-ethylene | H | Me | Me | $CH_2OH$ | H |
| 10 | 9 | 9 | OH | $CH_2$ | normal | single | E-ethylene | Me | H | Me | $CH_2OH$ | H |
| 11 | 10 | 9 | OH | $CH_2$ | normal | single | E-ethylene | H | Me | $CH_2OH$ | Me | H |
| 12 | 11 | 9 | OH | $CH_2$ | normal | single | E-ethylene | Me | H | $CH_2OH$ | Me | H |
| 13 | 12 | 9 | OH | $CH_2$ | normal | single | E-ethylene | H | Me | Me | $C(OH)Et_2$ | H |
| 14 | 13 | 9 | OH | $CH_2$ | normal | single | E-ethylene | H | Me | H | H | cyclopropyl |
| 15 | 14 | 8 | OH | $CH_2$ | normal | single | ethynylene | H | Me | Me | Me | H |
| 16 | 15 | 8 | OH | $CH_2$ | normal | single | ethynylene | Me | H | $C(OH)Me_2$ | bond | bond |
| 17 | 16 | 8 | OH | $CH_2$ | normal | single | ethynylene | H | Me | $C(OH)Et_2$ | bond | bond |
| 18 | 17 | 8 | OH | $CH_2$ | normal | single | ethynylene | Me | H | $C(OH)Et_2$ | bond | bond |
| 19 | | | OH | $CH_2$ | normal | single | ethynylene | H | Me | $CMe_3$ | bond | bond |
| 20 | | | OH | $CH_2$ | normal | single | ethynylene | Me | H | $CMe_3$ | bond | bond |
| 21 | 19 | | F | $CH_2$ | normal | single | E-ethylene | H | Me | Me | Me | H |
| 22 | 20 | | OH | $H_2$ | normal | single | E-ethylene | H | Me | Me | Me | H |
| 23 | 21 | | OH | $CH_2$ | epi | single | E-ethylene | H | Me | Me | Me | H |
| 24 | 22 | | OH | $CH_2$ | normal | double | E-ethylene | H | Me | Me | Me | H |
| 25 | 23 | 8 | OH | $CH_2$ | normal | single | E-ethylene | H | Me | $CF_3$ | $CF_3$ | H |
| 26 | | | H | $CH_2$ | normal | single | E-ethylene | H | Me | Me | $CH_2OH$ | H |
| 27 | 25 | 8 | OH | $CH_2$ | normal | single | E-ethylene | H | Me | Br | Br | H |
| 28 | 26 | 8 | OH | $CH_2$ | normal | single | E-ethylene | H | Me | Et | Et | H |
| 29 | 27 | 8 | OH | $CH_2$ | epi | single | E-ethylene | H | Me | Et | Et | H |
| 30 | 28 | 9 | OH | $CH_2$ | normal | single | E-ethylene | H | Me | —$(CH_2)_3$— | | Me |
| 31 | 29 | 8 | OH | $CH_2$ | normal | single | E-ethylene | H | Me | Cl | Cl | H |
| 32 | 30 | 9 | OH | $CH_2$ | normal | single | E-ethylene | H | Me | —$(CH_2)_4$— | | H |

TABLE 1-continued

| Compound | Example Number | General Procedure | A | B | 3-Configuration | 16,17-bond | X | Y | Z | R1 | R2 | R3 |
|---|---|---|---|---|---|---|---|---|---|---|---|---|
| 33 | 31 | 9 | OH | CH₂ | normal | single | E-ethylene | H | Me | | —(CH₂)₅— | H |
| 34 | 32 | 9 | OH | CH₂ | normal | single | bond | Me | H | | —(CH₂)₂— | H |
| 35 | 33 | 9 | OH | CH₂ | normal | single | bond | H | Me | | —(CH₂)₂— | H |
| 36 | 36 | 8 | OH | CH₂ | normal | single | E-ethylene | Me | H | CF₃ | CF₃ | H |

TABLE 2

| Entry | Compound number | Type (Scheme 1) | Preparation Number | General Procedure | A* | B | 3-Configuration | 16,17-bond | Y | Z | Ethylene configuration | R1 | R2 | R3 | W |
|---|---|---|---|---|---|---|---|---|---|---|---|---|---|---|---|
| 1 | 101 | 1a | | | O-TBS | | normal | single | H | Me | | | | | |
| 2 | 102 | 1c | | | | | | single | H | Me | | | | | |
| 3 | 103 | 1a | | | O-TBS | | normal | single | Me | H | | | | | |
| 4 | 104 | 1a | | | O-TBS | | normal | double | H | Me | | | | | |
| 5 | 202 | 2a | | | O-TBS | | normal | single | H | Me | | | | | H |
| 6 | 203 | 2a | | | O-TBS | | normal | single | Me | H | | | | | H |
| 7 | 204 | 2a | | | O-TBS | | normal | single | H | Me | E | | | | cyclopropyl |
| 8 | 205 | 2a | 35 | | O-TBS | | normal | single | H | Me | E | | | | Me |
| 9 | 206 | 2c | | | | | | single | H | Me | | | | | H |
| 10 | 301 | 3a | | | O-TBS | | normal | single | H | Me | E | | | H | SO₂—Ph |
| 11 | 302 | 3a | 33 | | O-TBS | | normal | single | H | Me | E | | | H | P(O)Ph₂ |
| 12 | 401 | 4a | | | O-TBS | | normal | single | H | Me | | | | H | SO₂—Ph |
| 13 | 402 | 4a | | | O-TBS | | normal | single | H | Me | | | | H | P(O)Ph₂ |
| 14 | 403 | 4a | | | O-TBS | | normal | single | H | Me | | | | H | SeMe |
| 15 | 501 | 5a | 1 | 1 | O-TBS | | normal | single | H | Me | E | Me | Me | H | |
| 16 | 502 | 5a | 8 | 1 | O-TBS | | normal | single | H | Me | Z | Me | Me | H | |
| 17 | 503 | 5a | 3 | 1 | O-TBS | | normal | single | Me | H | E | Me | Me | H | |
| 18 | 504 | 5a | 4 | 1 | O-TBS | | normal | single | H | Me | E | —(CH₂)₂— | | H | |
| 19 | 505 | 5a | 5 | 1 | O-TBS | | normal | single | Me | H | E | —(CH₂)₂— | | H | |
| 20 | 506 | 5a | 6 | 1 | O-TBS | | normal | single | H | Me | E | —(CH₂)₃— | | H | |
| 21 | 507 | 5a | 7 | 1 | O-TBS | | normal | single | Me | H | E | —(CH₂)₃— | | H | |
| 22 | 508 | 5a | 9 | 2 | O-TBS | | normal | single | H | Me | E | Me | CO₂Et | H | |
| 23 | 509 | 5a | 9 | 2 | O-TBS | | normal | single | H | Me | E | CO₂Et | Me | H | |
| 24 | 510 | 5a | 11 | 3 | O-TBS | | normal | single | H | Me | E | Me | CH₂OH | H | |
| 25 | 511 | 5a | 12 | 3 | O-TBS | | normal | single | H | Me | E | CH₂OH | Me | H | |
| 26 | 512 | 5a | 10 | 2 | O-TBS | | normal | single | Me | H | E | Me | CO₂Et | H | |
| 27 | 513 | 5a | 10 | 2 | O-TBS | | normal | single | Me | H | E | CO₂Et | Me | H | |
| 28 | 514 | 5a | 13 | 3 | O-TBS | | normal | single | Me | H | E | Me | CH₂OH | H | |
| 29 | 515 | 5a | 14 | 3 | O-TBS | | normal | single | Me | H | E | CH₂OH | Me | H | |
| 30 | 516 | 5a | 15 | 4 | O-TBS | | normal | single | H | Me | E | Me | C(OH)Et₂ | H | |
| 31 | 517 | 5a | 16 | | O-TBS | | normal | single | H | Me | E | H | H | cyclopropyl | |
| 32 | 518 | 5a | 17 | | O-TBS | | normal | single | Me | H | E | Br | Br | H | |
| 33 | 534 | 5a | 34 | | O-TBS | | normal | single | H | Me | E | CF₃ | CF₃ | H | |
| 34 | 519 | 5b | 101 | 7 | O-TBS | CH₂ | normal | single | H | Me | E | Me | Me | H | |
| 35 | 520 | 5b | 114 | 7 | O-TBS | CH₂ | normal | single | Me | H | E | Br | Br | H | |
| 36 | 521 | 5b | 102 | 7 | O-TBS | CH₂ | normal | single | H | Me | Z | Me | Me | H | |
| 37 | 522 | 5c | 2 | 1 | | | | single | H | Me | E | Me | Me | H | |
| 38 | 523 | 5b | 103 | 7 | O-TBS | CH₂ | normal | single | Me | H | E | Me | Me | H | |
| 39 | 524 | 5b | 104 | 7 | O-TBS | CH₂ | normal | single | H | Me | E | —(CH₂)₂— | | H | |
| 40 | 525 | 5b | 105 | 7 | O-TBS | CH₂ | normal | single | Me | H | E | —(CH₂)₂— | | H | |
| 41 | 526 | 5b | 106 | 7 | O-TBS | CH₂ | normal | single | H | Me | E | —(CH₂)₃— | | H | |
| 42 | 527 | 5b | 107 | 7 | O-TBS | CH₂ | normal | single | Me | H | E | —(CH₂)₃— | | H | |
| 43 | 528 | 5b | 108 | 7 | O-TBS | CH₂ | normal | single | H | Me | E | Me | CH₂OH | H | |
| 44 | 529 | 5b | 109 | 7 | O-TBS | CH₂ | normal | single | H | Me | E | CH₂OH | Me | H | |
| 45 | 530 | 5b | 110 | 7 | O-TBS | CH₂ | normal | single | Me | H | E | Me | CH₂OH | H | |
| 46 | 531 | 5b | 111 | 7 | O-TBS | CH₂ | normal | single | Me | H | E | CH₂OH | Me | H | |
| 47 | 532 | 5b | 112 | 7 | O-TBS | CH₂ | normal | single | H | Me | E | Me | C(OH)Et₂ | H | |
| 48 | 533 | 5b | 113 | 7 | O-TBS | CH₂ | normal | single | H | Me | E | H | H | cyclopropyl | |
| 49 | 535 | 5b | 128 | 7 | O-TBS | CH₂ | normal | single | H | Me | E | CF₃ | CF₃ | H | |
| 50 | 601 | 6a | | | O-TBS | | normal | single | H | Me | | | | | |
| 51 | 602 | 6a | | | O-TBS | | normal | single | Me | H | | | | | |
| 52 | 701 | 7a | 18, 19 | 5 | O-TBS | | normal | single | H | Me | | | | | |
| 53 | 702 | 7a | 20 | 5 | O-TBS | | normal | single | Me | H | | | | | |
| 54 | 801 | 8a | 19 | 5 | O-TBS | | normal | single | H | Me | | | | | |
| 55 | 802 | 8a | 20 | 5 | O-TBS | | normal | single | Me | H | | | | | |
| 56 | 901 | 9a | 18 | 5 | O-TBS | | normal | single | H | Me | | Me | Me | H | |
| 57 | 1001 | 10a | 18 | 5 | O-TBS | | normal | single | H | Me | | Me | Me | H | |
| 58 | 1002 | 10b | 115 | 7 | O-TBS | CH₂ | normal | single | H | Me | | Me | Me | H | |

TABLE 2-continued

| Entry | Compound number | Type (Scheme 1) | Preparation Number | General Procedure | A* | B | 3-Configuration | 16,17-bond | Y | Z | Ethylene configuration | R1 | R2 | R3 | W |
|---|---|---|---|---|---|---|---|---|---|---|---|---|---|---|---|
| 59 | 1003 | 10a | 21 | 6 | O-TBS | | normal | single | Me | H | | C(OH)Me$_2$ | bond | bond | |
| 60 | 1004 | 10b | 116 | 7 | O-TBS | CH$_2$ | normal | single | Me | H | | C(OH)Me$_2$ | bond | bond | |
| 61 | 1005 | 10a | 22 | 6 | O-TBS | | normal | single | H | Me | | C(OH)Et$_2$ | bond | bond | |
| 62 | 1006 | 10b | 117 | 7 | O-TBS | CH$_2$ | normal | single | H | Me | | C(OH)Et$_2$ | bond | bond | |
| 63 | 1007 | 10a | 23 | 6 | O-TBS | | normal | single | Me | H | | C(OH)Et$_2$ | bond | bond | |
| 64 | 1008 | 10b | 118 | 7 | O-TBS | CH$_2$ | normal | single | Me | H | | C(OH)Et$_2$ | bond | bond | |
| 65 | 1009 | 10a | | 6 | O-TBS | | normal | single | H | Me | | CMe$_3$ | bond | bond | |
| 66 | 1010 | 10b | | 7 | O-TBS | CH$_2$ | normal | single | H | Me | | CMe$_3$ | bond | bond | |
| 67 | 1011 | 10a | | 6 | O-TBS | | normal | single | Me | H | | CMe$_3$ | bond | bond | |
| 68 | 1012 | 10b | | 7 | O-TBS | CH$_2$ | normal | single | Me | H | | CMe$_3$ | bond | bond | |
| 69 | 536 | 5a | 24 | | O-TBS | | normal | single | H | Me | E | Br | Br | H | |
| 70 | 538 | 5a | 25 | | O-TBS | | normal | single | H | Me | E | Cl | Cl | H | |
| 71 | 540 | 5a | 26 | | O-TBS | | normal | single | H | Me | E | —(CH$_2$)$_3$— | | Me | |
| 72 | 542 | 5a | 27 | 1 | O-TBS | | normal | single | H | Me | E | —(CH$_2$)$_4$— | | H | |
| 73 | 544 | 5a | 28 | 1 | O-TBS | | normal | single | H | Me | E | —(CH$_2$)$_5$— | | H | |
| 74 | 546 | | 29 | 1 | O-TBS | | normal | single | Me | H | bond | —(CH$_2$)$_2$— | | H | |
| 75 | 548 | | 30 | 1 | O-TBS | | normal | single | H | Me | bond | —(CH$_2$)$_2$— | | H | |
| 76 | 550 | 5a | 31 | | O-TBS | | normal | single | H | Me | E | Et | Et | H | |
| 77 | 303 | 5b | 32 | | O-TBS | CH$_2$ | epi | single | H | Me | E | | | | P(O)Ph$_2$ |
| 78 | 537 | 5b | 119 | 7 | O-TBS | CH$_2$ | normal | single | H | Me | E | Br | Br | H | |
| 79 | 539 | 5b | 120 | 7 | O-TBS | CH$_2$ | normal | single | H | Me | E | Cl | Cl | H | |
| 80 | 541 | 5b | 121 | 7 | O-TBS | CH$_2$ | normal | single | H | Me | E | —(CH$_2$)$_3$— | | Me | |
| 81 | 543 | 5b | 122 | 7 | O-TBS | CH$_2$ | normal | single | H | Me | E | —(CH$_2$)$_4$— | | H | |
| 82 | 545 | 5b | 123 | 7 | O-TBS | CH$_2$ | normal | single | H | Me | E | —(CH$_2$)$_5$— | | H | |
| 83 | 547 | | 124 | 7 | O-TBS | CH$_2$ | normal | single | Me | H | bond | —(CH$_2$)$_2$— | | H | |
| 84 | 549 | | 125 | 7 | O-TBS | CH$_2$ | normal | single | H | Me | bond | —(CH$_2$)$_2$— | | H | |
| 85 | 551 | 5b | 126 | 7 | O-TBS | CH$_2$ | normal | single | H | Me | E | Et | Et | H | |
| 86 | 552 | 5b | 127 | | O-TBS | CH$_2$ | epi | single | H | Me | E | Et | Et | H | |

PREPARATIONS AND EXAMPLES

Reactions were routinely (unless otherwise noted) run by stirring under an argon atmosphere, with additions of reagent (liquid or in solution) occurring drop wise via a syringe. As standard work-up procedure, the organic layer was separated, washed sequentially with water and saturated sodium chloride solution, dried over anhydrous magnesium sulphate, and concentrated in vacuo to give a crude product, which was then purified by chromatography. All preparative and analytical (TLC) chromatography was performed on silica gel using a gradient from 1% to 50% (v:v) ether (i.e. diethyl ether) in petroleum ether as eluent, or from 30% (v:v) ethyl acetate in petroleum ether to pure ethyl acetate. In the General Procedures, the variable entries are indented (on separate lines) and then listed in the specific Preparations, together with details if needed on any deviations from the General Procedure that were actually employed. However the proportional scaling of the quantities of non-variable reagents and solvents to the molar quantities specified in each Preparation is taken for granted and thus not considered a deviation requiring explicit details.

Compounds were characterised spectroscopically: For $^1$H nuclear magnetic resonance spectra (300 MHz) and $^{13}$C NMR (75.6 MHz) chemical shift values (δ) (in ppm) are quoted, unless otherwise specified, for deuteriochloroform solutions relative to internal tetramethylsilane (added, $^1$H-NMR: δ=0.00 ppm, $^{13}$C-NMR: δ=0.00 ppm) or chloroform (residual, $^1$H-NMR: δ=7.25 ppm) or deuteriochloroform ($^{13}$C-NMR: δ=76.81 ppm). The value for a multiplet ($^1$H-NMR), either defined [doublet (d), triplet (t), quartet (q)] or not (m) at the approximate mid point is given unless a range is quoted (s=singlet, b=broad). In some cases, only selected, characteristic signals may be reported for the intermediate compounds i.e. those of Table 2.

General Procedure 1 (Preparations 1-7 and 27-28) [2→5] (Preparations 29-30) [1→5]

To a solution or suspension, maintained at about −70° C., of an alkyl-triphenylphosphonium salt (7 mmol) in dry THF (50 ml) was added n-butyllithium (1.6M in hexanes, 4.36 ml, 7 mmol). The temperature of the mixture was then allowed to rise to 0° C. for 20 min, after which recooling at −70° C. was resumed for the addition of intermediate 1 or 2 (4 mmol), dissolved in dry THF (8 ml). After 30 minutes at the same temperature, slow warming up, and 70 min at room temperature, the mixture was partitioned between saturated ammonium chloride solution and ethyl acetate, and worked up according to the standard work-up procedure above to give intermediate 5.

Preparation 1: Compound 501

Alkyl-triphenylphosphonium salt: Isopropyl-triphenylphosphonium iodide (3.16 g, 7.3 mmol).

Intermediate 2: 202 (2.39 g).

Purification of compound 502 from the crude product by direct crystallisation from methanol, omitting the chromatography step: $^{13}$C-NMR: δ=153.5, 143.1, 138.1, 135.2, 132.5, 125.1, 124.1, 121.5, 116.3, 106.4, 70.0, 67.1, 56.3, 56.2, 45.7, 43.8, 40.4, 40.3, 36.4, 28.8, 27.7, 25.7, 25.6, 23.3, 22.0, 20.6, 18.1, 18.0, 17.9, 12.1, −4.9, −5.1 ppm.

Preparation 2: Compound 522

Alkyl-triphenylphosphonium salt: Isopropyl-triphenylphosphonium iodide (1.55 g, 3.6 mmol).

Intermediate 2: 206 (Prepared from 102 analogously to the described preparation of 202 from 101 in WO9100855) (0.7 g, 2 mmol).

Compound 522: $^{13}$C-NMR: δ=138.5, 132.3, 125.1, 123.8, 69.3, 56.4, 52.9, 42.0, 40.5, 39.7, 34.3, 29.2, 25.7, 25.6, 22.8, 20.3, 18.0, 17.8, 17.5, 13.8, −5.0, −5.3 ppm.

Preparation 3: Compound 503
Alkyl-triphenylphosphonium salt: Isopropyl-triphenylphosphonium iodide (1.47 g, 3.4 mmol).
Intermediate 2: 203 (1 g, 1.67 mmol).
Purification of compound 503 by chromatography (2% v:v, ether in petroleum ether).
Compound 503: $^{13}$C-NMR: δ=153.4, 143.3, 138.5, 135.1, 132.3, 125.1, 124.0, 121.6, 116.1, 106.4, 70.1, 67.0, 56.7, 56.1, 45.8, 43.8, 40.6, 39.6, 36.4, 28.8, 27.1, 25.7, 25.7, 25.6, 23.3, 21.9, 21.3, 18.1, 17.9, 12.1, −4.9, −5.1 ppm.

Preparation 4: Compound 504
Alkyl-triphenylphosphonium salt: Cyclopropyl-triphenylphosphonium bromide (0.76 g, 2 mmol).
Intermediate 2: 202 (0.60 g, 1 mmol)
Purification of compound 504 by chromatography (5% v:v, ether in petroleum ether).
Compound 504: $^{13}$C-NMR: δ=6.45 (d, J=12 Hz, 1H), 6.33 (bd, J=10 Hz, 1H), 6.12 (dd, J=15 Hz, J=10 Hz, 1H), 5.81 (d, J=12 Hz, 1H), 5.55 (dd, J=9 Hz, J=15 Hz, 1H), 4.97 (m, 1H), 4.93 (m, 1H), 4.53 (m, 1H), 4.23 (m, 1H), 2.86 (m, 1H), 2.55 (dd, 1H), 2.30 (bd, 1H), 2.20-1.15 (m, 14H), 1.15-1.0 (m, 14H), 1.07 (d, J=7 Hz, 3H), 0.89 (s, 9H), 0.86 (s, 9H), 0.57 (s, 3H), 0.05 (m, 12H) ppm.

Preparation 5: Compound 505
Alkyl-triphenylphosphonium salt: Cyclopropyl-triphenylphosphonium bromide (1.53 g, 4 mmol).
Intermediate 2: 203 (0.56 g, 0.93 mmol)
Purification of compound 505 by chromatography (5% v:v, ether in petroleum ether).
Compound 505: $^{13}$C-NMR: δ=6.44 (d, J=11.4 Hz, 1H), 6.35 (bd, J=10.3 Hz, 1H), 6.08 (dd, J=10.3 Hz, J=15.3 Hz, 1H), 5.81 (d, J=11.4 Hz, 1H), 5.55 (dd, J=9.5 Hz, J=15.3 Hz, 1H), 4.97 (bt, 1H), 4.93 (bt, 1H), 4.52 (m, 1H), 4.21 (m, 1H), 2.84 (m, 1H), 2.54 (dd, J=5.3 Hz, J=14.5 Hz, 1H), 2.31 (bd, J=13.7 Hz, 1H), 2.2-1.0 (m, 18H), 0.97 (d, J=6.5 Hz, 3H), 0.89 (s, 9H), 0.86 (s, 9H), 0.52 (s, 3H), 0.05 (s, 12H) ppm.

Preparation 6: Compound 506
Alkyl-triphenylphosphonium salt: Cyclobutyl-triphenylphosphonium bromide (0.80 g, 2 mmol).
Intermediate 2: 202 (0.60 g, 1 mmol)
Purification of compound 506 by chromatography (1% v:v, ether in petroleum ether).
Compound 506: $^{13}$C-NMR: δ=153.5, 143.1, 142.5, 137.1, 135.2, 123.6, 121.5, 120.8, 116.3, 106.4, 70.0, 67.0, 56.3, 56.2, 45.7, 43.8, 40.3, 40.3, 36.4, 31.1, 29.7, 28.7, 27.7, 25.7, 25.6, 23.3, 22.0, 20.5, 18.1, 17.9, 17.0, 12.0, −4.9, −5.0, −5.1 ppm.

Preparation 7: Compound 507
Alkyl-triphenylphosphonium salt: Cyclobutyl-triphenylphosphonium bromide (1.33 g, 3.34 mmol).
Intermediate 2: 203 (1 g, 1.67 mmol).
Purification of compound 507 by chromatography (1% v:v, ether in petroleum ether).
Chromatography: 1% ether in petroleum ether.
Compound 507: $^{13}$C-NMR: δ=153.4, 143.3, 142.4, 137.4, 135.1, 123.6, 121.6, 120.9, 116.1, 106.4, 70.1, 67.0, 56.8, 56.1, 45.8, 43.8, 40.6, 39.6, 36.4, 31.1, 29.7, 28.8, 27.1, 25.7, 25.6, 23.3, 21.9, 21.3, 18.1, 17.9, 16.9, 12.1, −4.9, −5.1 ppm.

Preparation 8: Compound 502 [4→5]
To a solution, maintained at about −70° C., of the lithio-derivative 403 (Table 2., entry 14) (prepared from 0.75 g, 1 mmol of the seleno-acetal derivative of 101 in dry THF (5 ml)) was added dropwise the side chain building block 3-methyl-crotonaldehyde (0.10 g, 1.2 mmol). After stirring at the same temperature for 30 min, the reaction was quenched with wet THF and the mixture partitioned between ether and water and to give the intermediate adduct as a mixture of diastereoisomers. To a solution of this, maintained at about 5° C., in dry DCM (15 ml) and triethylamine (2 ml) was added methanesulphonyl chloride (1.5 mmol). After stirring at the same temperature for 30 min, the reaction mixture was partitioned between ether and water. The standard work-up procedure above gave compound 502: $^{13}$C-NMR: δ=153.5, 143.1, 136.0, 135.2, 134.4, 121.7, 121.5, 120.4, 116.3, 106.4, 70.0, 67.0, 56.5, 56.3, 45.7, 43.8, 40.4, 40.3, 36.4, 28.8, 27.3, 25.7, 25.6, 23.4, 22.0, 20.6, 18.0, 17.9, 12.2, −4.9, −5.0, −5.1 ppm.

General Procedure 2 (Preparations 9, 10) [2→5]
To a solution, maintained at about 20° C., of Intermediate 2 (0.76 mmol) in DCM (5 ml) was added triethyl 2-phosphonopropionate (0.45 g, 1.9 mmol), 50% aqueous NaOH solution (5 ml), and TBA hydrogen sulphate (0.11 g). After vigorous stirring for 105 min, the reaction mixture partitioned between water and ethyl acetate. Standard work-up as above (chromatography 2%-5% v:v ethyl acetate in petroleum ether as eluent) gave Intermediates 5.

Preparation 9: Compound 508 and 509
Intermediate 2: 202 (0.46 g).
First eluted product: compound 509: $^{13}$C-NMR: δ=167.6, 153.5, 147.6, 142.8, 141.1, 135.3, 125.3, 123.8, 121.5, 116.4, 106.3, 70.0, 67.0, 59.9, 56.2, 55.8, 45.8, 43.8, 40.3, 40.3, 36.4, 28.7, 27.5, 25.7, 25.6, 23.3, 22.1, 20.4, 20.0, 18.1, 17.9, 14.1, 12.1, −5.0, −5.1 ppm; Second eluted product: compound 508: $^{13}$C-NMR: δ=168.5, 153.5, 148.7, 142.7, 138.7, 135.4, 124.9, 123.5, 121.5, 116.4, 106.4, 70.0, 67.0, 60.2, 56.1, 55.7, 45.8, 43.8, 40.8, 40.2, 36.4, 28.7, 27.5, 25.7, 25.6, 23.3, 22.1, 20.0, 18.1, 17.9, 14.1, 12.4, 12.1, −5.0, −5.1 ppm.

Preparation 10: Compound 512 and 513
Intermediate 2: 203 (1 g, 1.68 mmol).
First eluted product: compound 513: $^{13}$C-NMR: δ=167.6, 153.4, 148.1, 143.0, 140.8, 135.2, 125.2, 123.8, 121.5, 116.2, 106.4, 70.0, 67.0, 59.9, 56.6, 56.0, 45.8, 43.8, 40.7, 39.6, 36.4, 28.7, 27.0, 25.7, 25.6, 23.2, 21.8, 20.6, 20.5, 18.1, 17.9, 14.1, 12.1, −4.9, −5.1 ppm; Second eluted product: compound 512: $^{13}$C-NMR: δ=168.5, 153.4, 149.3, 142.9, 138.5, 135.3, 124.9, 123.4, 121.5, 116.3, 106.5, 70.1, 67.0, 60.2, 56.5, 56.0, 45.7, 43.8, 41.1, 39.6, 36.4, 28.7, 27.0, 25.7, 25.6, 23.2, 21.8, 20.7, 18.0, 17.9, 14.2, 12.4, 12.2, −5.0, −5.1, −5.1 ppm.

General Procedure 3 (Preparations 11 to 14) [5→5']
To a solution, maintained at about −70° C., of the ester 5 (0.34 mmol) in dry THF (5 ml) was added DIBAL (1M in hexanes, 1 ml, 1 mmol). After 30 min at the same temperature, the temperature of the mixture was then allowed to rise to −20° C. over 1 h, after which recooling at −70° C. was resumed for the addition of methanol (0.5 ml) to quench the reaction. The mixture was then partitioned between water and ethyl acetate, and worked up according to the standard procedure above to give the alcohol 5'.

Preparation 11: Compound 510
Intermediate 5: 508 (0.23 g).
Compound 510: $^{13}$C-NMR: δ=153.5, 142.9, 141.2, 135.3, 134.5, 125.4, 123.3, 121.5, 116.3, 106.4, 70.0, 68.6, 67.0, 56.2, 56.1, 45.7, 43.8, 40.4, 40.3, 36.4, 28.7, 27.7, 25.7, 25.6, 23.3, 22.0, 20.4, 18.1, 17.9, 13.9, 12.1, −4.9, −5.1 ppm.

Preparation 12: Compound 511
Intermediate 5: 509 (0.18 g, 0.26 mmol).
Compound 511: $^{13}$C-NMR: δ=153.5, 142.9, 140.8, 135.3, 134.0, 128.3, 122.7, 121.5, 116.3, 106.4, 70.1, 67.0, 61.7, 56.2, 56.1, 45.7, 43.8, 40.3, 36.4, 28.7, 27.6, 25.7, 25.6, 25.4, 23.3, 22.0, 21.2, 20.3, 18.0, 17.9, 12.1, −5.0, −5.1 ppm.

Preparation 13: Compound 514
Intermediate 5: 512 (0.36 g, 0.53 mmol).
Compound 514: $^{13}$C-NMR: δ=153.4, 143.1, 141.6, 135.1, 134.3, 125.4, 123.2, 121.5, 116.2, 106.5, 70.1, 68.6, 67.0, 56.7, 56.1, 45.8, 43.8, 40.7, 39.6, 36.4, 28.8, 27.1, 25.7, 25.6, 23.2, 21.9, 21.1, 18.0, 17.9, 13.9, 12.1, −5.0, −5.1 ppm.

Preparation 14: Compound 515

Intermediate 5: 513 (0.23 g).

Compound 515: $^{13}$C-NMR: δ=153.4, 143.1, 141.3, 135.2, 133.9, 128.3, 122.6, 121.5, 116.2, 106.5, 70.1, 67.0, 61.7, 56.7, 56.1, 45.8, 43.8, 40.6, 39.6, 36.4, 28.8, 27.1, 25.7, 25.6, 23.2, 21.9, 21.2, 21.0, 18.0, 17.9, 12.1, −4.9, −5.1 ppm.

General Procedure 4 (Preparation 15) [5→5']

To a solution, maintained at about −70° C., of the ester 5 (0.6 mmol) in dry THF (5 ml) was added the alkyl-lithium. After 1 h at the same temperature, the reaction was quenched with methanol (0.5 ml), and the mixture partitioned between ether and water. Standard work-up gave the alcohol 5.

Preparation 15: Compound 516 [5→5']

Intermediate 5: 508 (0.4 g).

Alkyl-lithium: Ethyl-lithium (0.8 M in diethyl ether, 2 ml).

Compound 516: $^{13}$C-NMR: δ=153.5, 143.0, 140.1, 137.3, 135.2, 124.4, 123.8, 121.5, 116.3, 106.4, 78.2, 70.1, 67.0, 56.3, 56.2, 45.8, 43.8, 40.4, 40.3, 36.4, 31.6, 28.8, 27.6, 25.7, 25.6, 23.3, 22.0, 20.4, 18.1, 17.9, 13.3, 12.1, 7.4, −4.9, −5.1 ppm.

Preparation 16: Compound 517 [2→5]

To a solution/suspension, maintained at about 5° C., of compound 204 (0.32 g, 0.5 mmol) and methyl-triphenylphosphonium bromide (0.59 g, 1.57 mmol) in dry THF (5 ml) was added potassium tert-butoxide (1M solution in THF, 1.4 ml). After 2 h at the same temperature, the mixture was partitioned between water and ether, and worked up as standard to give Compound 517, recrystallised from ether-methanol: $^{13}$C-NMR: δ=153.5, 147.6, 143.0, 136.8, 135.3, 129.6, 121.5, 116.3, 110.3, 106.4, 70.0, 67.0, 56.3, 45.8, 43.8, 40.3, 40.2, 36.4, 28.8, 27.5, 25.7, 25.6, 23.3, 22.0, 20.4, 18.1, 17.9, 12.6, 12.1, 5.3, 5.2, −5.0, −5.1 ppm.

Preparation 17: Compound 518 [2→5]

Tetrabromomethane (288 mg, 0.87 mmol) was dissolved in dry THF (3.6 ml).

Triphenylphosphine (456 mg 1.74 mmol) was added and the reaction mixture stirred for 30 minutes at room temperature. A solution of Compound 203 (261 mg; 0.435 mmol) and triethylamine (0.06 ml; 0.43 mmol) in THF (3.2 ml) was added. The reaction mixture was stirred for 90 minutes at room temperature, quenched with water (15 ml) and filtered through Decalite filter aid. The filter was washed with pentane (2×25 ml). The filtrate was extracted with water (3×15 ml) and saturated aqueous sodium chloride (15 ml), dried and concentrated in vacuo. The residue was purified by chromatography (0.5% ether in petroleum ether). 518: $^{13}$C-NMR: δ 153.4, 145.7, 142.8, 137.0, 135.3, 124.6, 121.5, 116.3, 106.5, 88.1, 70.1, 67.0, 56.4, 56.0, 45.7, 43.8, 40.8, 39.6, 36.4, 29.5, 28.7, 27.0, 25.7, 25.6, 25.4, 23.1, 21.8, 20.5, 18.1, 17.9, 12.1, −5.0, −5.1 ppm.

General Procedure 5 (Preparations 18, 19, 20) [6-7→9→10, including 6→7-8]

To a solution, maintained at about −70° C., of the dichloro-intermediate 6 (1 mmol) in dry THF (5 ml) was added n-butyl-lithium (1.33 ml, 1.5M in hexanes, 2 molar eq.). The temperature of the mixture was then allowed to rise to 0° C. momentarily to ensure effective conversion to the intermediate lithio-derivative 7. Quenching by partitioning between saturated ammonium chloride solution and ether, and work up at this stage mixture gave intermediate 8. Alternatively recooling of the solution of 7 at −70° C. was resumed, and addition of a carbonyl compound (1.5 mmol), was made. After 30 minutes at the same temperature and slow warming up to room temperature, the mixture was partitioned between saturated ammonium chloride solution and ether, and worked up as standard to give compound 9.

To a solution of, maintained at about 5° C., of this intermediate alcohol 9 (ca. 0.4 mmol) in dry dichloromethane (8 ml) was added Martin's sulfurane (0.54 g, 2 molar equiv.).

After stirring at the same temperature for 1 h, the reaction mixture was partitioned between ether and 20% sodium hydroxide solution. Standard work-up gave the Product 10.

Preparation 18: Compound 1001 via Intermediate 701 and Compound 901

Intermediate 6: 601 (0.62 g, 0.97 mmol).

Carbonyl compound: Isobutyraldehyde (0.13 ml).

Compound 901: $^{13}$C-NMR: δ=153.5, 142.6, 135.4, 121.4, 116.4, 106.4, 90.4, 80.3, 70.0, 68.0, 67.0, 55.9, 55.8, 45.6, 43.8, 39.5, 36.4, 34.5, 28.7, 27.6, 26.3, 25.7, 25.6, 23.1, 22.0, 21.4, 18.1, 18.0, 17.9, 17.2, 12.4, −5.0, −5.1 ppm.

Intermediate 9: 901 (0.27 g).

The product 10 was further purified by crystallisation from ether-methanol.

Compound 1001: $^{13}$C-NMR: δ=153.4, 146.0, 142.8, 135.3, 121.5, 116.4, 106.5, 105.4, 96.5, 78.9, 70.1, 67.0, 56.1, 56.0, 45.6, 43.8, 39.6, 36.4, 28.7, 28.4, 26.4, 25.7, 25.6, 24.4, 23.1, 22.1, 21.6, 20.6, 18.1, 17.9, 12.3, −5.0, −5.1, −5.1 ppm.

Preparation 19: Compound 801 via Intermediate 701

Intermediate 6: 601 (0.64 g).

Compound 801: $^{13}$C-NMR: δ=153.4, 142.6, 135.4, 121.4, 116.5, 106.5, 89.0, 70.1, 68.4, 67.0, 55.9, 55.5, 45.6, 43.8, 39.6, 36.4, 28.7, 27.6, 26.4, 25.7, 25.6, 23.1, 22.0, 21.2, 18.1, 17.9, 12.1, −4.9, −5.1, −5.1 ppm.

Preparation 20: Compound 802 via Intermediate 702

Intermediate 6: 602 (0.66 g).

Compound 802: $^{13}$C-NMR: δ=153.4, 142.9, 135.3, 121.5, 116.3, 106.5, 89.1, 70.1, 69.0, 67.1, 56.0, 55.4, 45.8, 43.8, 39.5, 36.4, 28.8, 27.3, 25.7, 25.6, 23.2, 21.7, 20.8, 18.1, 17.9, 12.1, −4.9, −5.1-5.1 ppm.

1-Bromo-3-hydroxy-3-ethyl-pentyne

To a solution of 3-hydroxy-3-ethyl-1-pentyne (20 mmol) in dry THF (40 ml) at room temperature was added n-butyl-lithium (42 mmol, 1.6M in hexanes) during 10 minutes. After stirring for 30 minutes, the solution was cooled to −40° C. and a solution of bromine (1.13 ml, 3.52 g, 22 mmol) in dry THF (20 ml), also cooled to −40° C., was added, during 20 minutes, followed by re-heating to 25° C., during about 1 hour. Standard work-up after addition of ether and water (chromatography: 0% to 10% ether in petroleum ether) gave the title compound.

1-Bromo-3-hydroxy-3-methyl-1-butyne

When 3-hydroxy-3-methyl-1-butyne was used as starting material in the above preparation the product was 1-bromo-3-hydroxy-3-methyl-1-butyne. This was also prepared from 3-hydroxy-3-methyl-1-butyne by treatment at room temperature of an acetone solution with silver nitrate (0.3 eq.) and then, after 20 min, N-bromosuccinimide (1 molar equiv.). After 12 h ether was added, the solution filtered, and the filtrate worked-up as standard to give an oil that was distilled (b.p. 67° C./18 mmHg): $^{13}$C-NMR: δ=31.0, 31.0, 42.6, 66.1, 84.3 ppm.

General Procedure 6 (Preparations 21 to 23) [8→10]

To a solution, maintained at about 25° C., in dry pyrrolidine (5 ml) of the Intermediate 8 (0.2 mmol) was added the side chain building block (0.8 mmol; 4 molar equiv.), CuI 4 mg; 0.1 molar equiv.) and bis-triphenylphosphine-palladium dichloride (7 mg; 0.05 molar equiv.). After stirring at the same temperature for 17 h, the reaction mixture was partitioned between ether and saturated ammonium chloride solution and worked up as standard to give 10.

Preparation 21: Compound 1003

Intermediate 8: 802 (66 mg, 0.11 mmol).

Side chain building block: 1-Bromo-3-hydroxy-3-methyl-1-butyne (75 mg).

Compound 1003: $^{13}$C-NMR: δ=153.4, 142.7, 135.4, 121.4, 116.3, 106.5, 85.6, 80.4, 70.1, 67.2, 67.0, 65.4, 65.2, 55.8, 55.4, 45.7, 43.8, 39.2, 36.4, 31.0, 28.8, 28.0, 27.2, 25.7, 25.6, 23.3, 21.7, 20.3, 18.1, 17.9, 12.2, −5.0, −5.1, −5.1 ppm.

Preparation 22: Compound 1005

Intermediate 8: 801 (114 mg).

Side chain building block: 1-bromo-3-hydroxy-3-ethyl-1-pentyne.

Compound 1005: $^{13}$C-NMR: δ=153.4, 142.4, 135.5, 121.4, 116.5, 106.5, 85.0, 78.5, 72.5, 70.1, 69.3, 67.0, 64.9, 55.8, 55.6, 45.7, 43.7, 39.5, 36.4, 34.1, 28.6, 28.3, 26.3, 25.7, 25.6, 23.1, 22.0, 20.7, 18.1, 17.9, 12.2, 8.3, −5.0, −5.1, −5.1 ppm.

Preparation 23: Compound 1007

Intermediate 8: 802 (118 mg).

Side chain building block: 1-bromo-3-hydroxy-3-ethyl-1-pentyne.

Compound 1007: $^{13}$C-NMR: δ=153.4, 142.7, 135.4, 121.4, 116.3, 106.5, 85.0, 78.8, 72.5, 70.1, 69.2, 67.0, 65.4, 55.8, 55.4, 45.7, 43.8, 39.2, 36.4, 34.1, 28.8, 27.9, 27.1, 25.7, 25.6, 23.3, 21.7, 20.2, 18.1, 17.9, 12.2, 8.3, −5.0, −5.1, −5.1 ppm.

Preparation 24: Compound 536 [2→5]

Tetrabromomethane (8789 mg, 2.65 mmol) was dissolved in dry THF (9 ml). Triphenylphosphine (1800 mg, 6.8 mmol) was added and the reaction mixture stirred for 30 minutes at room temperature. A solution of compound 202 (794 mg, 1.32 mmol) and triethylamine (0.18 ml; 1.4 mmol) in THF (8 ml) was added. The reaction mixture was stirred for 90 minutes at room temperature, quenched with saturated aqueous hydrogen carbonate (15 ml) and filtered through Decalite filter aid. The filter was washed with pentane (2×25 ml). The filtrate was extracted with water (3×15 ml) and saturated aqueous sodium chloride (15 ml), dried and concentrated in vacuo. The residue was purified by chromatography (1.5% ether in petroleum ether) and crystallised from ether-methanol.

Compound 536: $^1$H-NMR: δ=6.86 (d,1H,J=9.9 Hz), 6.45 (d,1H), 6.02 (dd,1H,J=9.9 Hz and 15.3 Hz), 5.82 (d,1H), 5.76 (dd,1H, J=8.8 Hz and 15.3 Hz), 4.98 (m,1H), 4.94 (m,1H), 4.53 (m,1H), 4.21 (m,1H), 2.87 (m,1H), 2.55 (dd,1H), 2.30 (bd,1H), 2.18 (m,1H), 2.10-1.00 (m,13H), 1.07 (d,3H), 0.89 (s,9H), 0.86 (s,9H), 0.56 (s,3H), 0.08-0.01 (m,12H) ppm.

Preparation 25: Compound 538 [2→5]

Compound 202 (599 mg, 1 mmol) and bromotrichloromethane (0.095 ml, 1 mmol) were dissolved in DCM (30 ml) and cooled to −20 C. While maintaining the temperature between −20 and −10 C a solution of tris(dimethylamino)phosphine (0.40 ml, 2.2 mmol) in DCM (30 ml) was added dropwise. After stirring 30 minutes at room temperature pentane (150 ml) and water (30 ml) were added. The organic layer was isolated, washed with water (3×25 ml), and saturated aqueous sodium chloride (25 ml), dried, concentrated in vacuo and purified by chromatography (1% ether in petroleum ether).

Compound 538: $^1$H-NMR: δ=6.45 (d,1H), 6.34 (d,1H, J=10.3 Hz), 6.10 (dd,1H,J=10.3 Hz and 15.0 Hz) 5.82 (d,1H), 5.69 (dd,1H,J=8.8 Hz and 15.0 Hz), 4.98 (m,1H), 4.94 (m,1H), 4.53 (m,1H), 4.21 (m,1H), 2.87 (m,1H), 2.55 (dd, 1H), 2.30 (bd,1H), 2.19 (m,1H), 2.10-1.13 (m,13H), 1.07 (d,3H), 0.89 (s,9H), 0.86 (s,9H), 0.56 (s,3H), 0.08-0.02 (m,12H) ppm.

Preparation 26: Compound 540 [2-5]

Cyclobutyltriphenylphosphonium bromide (516 mg, 1.3 mmol) was suspended in dry THF (4.5 ml) and cooled to −6 C. n-Butyl lithium (1.6 M in hexane, 1.0 ml, 1.6 mmol) was added, the reaction mixture stirred for 20 minutes at room temperature, and then again cooled to −6° C. A solution of Compound 205 (400 mg, 0.65 mmol) and tris(2-(2-methoxyethoxy)ethyl)amine (42 µl, 0.13 mmol) was added and the reaction mixture stirred at room temperature for 3 hours. Water (20 ml) and petroleum ether (100 ml) were added. The organic layer was isolated, washwed with water (3×20 ml) and aqueous saturated sodium chloride (20 ml), dried, concentrated in vacuo, and purified by chromatography (0.5% ether in petroleum ether).

Compound 540: $^1$H-NMR: δ=6.46 (d,1H), 6.00 (d,1H, J=15.7 Hz), 5.81 (d,1H), 5.33 (dd,1H, J=8.8 Hz and 15.7 Hz), 4.98 (t,1H), 4.93 (t,1H), 4.53 (m,1H), 4.21 (m,1H), 2.87 (m,1H), 2.73 (m,4H), 2.55 (dd,1H), 2.30 (m,1H), 2.22-1.00 (m,16H), 1.56 (bs,3H), 1.05 (d,3H), 0.89 (s,9H), 0.86 (s,9H), 0.56 (s,3H), 0.10-0.02 (m,12H) ppm.

Preparation 27: Compound 542

Alkyl-triphenylphosphonium salt: Cyclopentyl-triphenylphosphonium bromide (1.40 g, 3.4 mmol).

Intermediate 2: 202 (1 g, 1.67 mmol).

Purification of compound 542 by chromatography (2% v:v, ether in petroleum ether).

Compound 542: $^1$H-NMR: δ=6.45 (d,1H), 6.02 (dd,1H, J=11.1 Hz and 14.9 Hz), 5.87 (m,1H), 5.81 (d,1H), 5.37 (dd,1H,J=8.8 Hz and 11.1 Hz), 4.98 (t,1H), 4.94 (t,1H), 4.53 (m,1H), 4.21 (m,1H), 2.87 (m,1H), 2.55 (dd,1H), 2.37-2.24 (m,5H), 2.20-1.86 (m,4H), 1.83-0.80 (m,14H), 1.05 (d,3H), 0.90 (s,9H), 0.86 (s,9H), 0.56 (s,3H), 0.08-0.03 (m,12H) ppm.

Preparation 28: Compound 544

Alkyl-triphenylphosphonium salt: Cyclohexyl-triphenylphosphonium bromide (1.44 g, 3.4 mmol).

Intermediate 2: 202 (1 g, 1.67 mmol).

Purification of compound 544 by chromatography (2% v:v, ether in petroleum ether).

Compound 544: $^1$H-NMR: δ=6.45 (d,1H), 6.20 (dd,1H, J=10.7 Hz and 14.9 Hz), 5.81 (d,1H), 5.70 (d,1H,J=10.7 Hz), 5.43 (dd,1H,J=8.4 Hz and 14.9 Hz), 4.97 (m, H), 4.93 (m,1H), 4.53 (m,1H), 4.21 (m,1H), 2.86 (m,1H), 2.56 (dd,1H), 2.35-0.80 (m,25H), 1.04 (d,3H), 0.89 (s,9H), 0.86 (s,9H), 0.56 (s,3H), 0.08-0.02 (m,12H) ppm.

Preparation 29: Compound 546

Alkyl-triphenylphosphonium salt: Cyclopropyl-triphenylphosphonium bromide (766 mg, 2 mmol).

Intermediate 1: Compound 103 (573 g, 1 mmol).

Purification by chromatography (2% v:v, ether in petroleum ether) to give 1(S),3(R)-bis(tert-butyldimethylsilyloxy)-20(R)-cyclopropylidenemethyl-9,10-seco-pregna-5(E),7(E),10(19)-triene (compound 546).

Compound 546: $^{13}$C-NMR: δ=153.4, 143.3, 135.0, 125.0, 121.6, 117.7, 116.1, 106.4, 70.1, 67.0, 56.8, 56.0, 45.7, 43.8, 39.7, 39.6, 36.4, 28.8, 27.1, 25.7, 25.6, 23.3, 21.9, 20.7, 18.0, 17.9, 12.2, 1.8, 1.7, −4.9, −5.0, −5.1, −5.1 ppm.

Preparation 30: Compound 548

Alkyl-triphenylphosphonium salt: Cyclopropyl-triphenylphosphonium bromide (606 mg, 1.6 mmol).

Intermediate 1: Compound 101 (458 g, 0.8 mmol).

Purification by chromatography (2% v:v, ether in petroleum ether) to give 1(S),3(R)-bis(tert-butyldimethylsilyloxy)-20(S)-cyclopropylidenemethyl-9,10-seco-pregna-5(E),7(E),10(19)-triene (compound 548).

Compound 548: $^{13}$C-NMR: δ=153.4, 143.2, 135.1, 124.4, 121.6, 118.2, 116.2, 106.4, 70.1, 67.0, 56.6, 56.3, 45.7, 43.8, 40.2, 39.6, 36.4, 28.8, 27.4, 25.7, 25.6, 23.4, 22.1, 20.3, 18.1, 17.9, 12.0, 2.2, 1.7, −4.9, −5.0, −5.1 ppm.

Preparation 31: Compound 550

To a solution, maintained at about −70° C., of the lithio-derivative 302 (prepared from the precursor 24-diphenylphosphinoyl-1(S),3(R)-di-TBS-oxy-9,10-seco-chola-5(E),7(E),10(19),22(E)-tetra-ene (0.21 g, 0.27 mmol) and n-butyl-lithium (0.55 ml)) in dry THF (2 ml)) was added dropwise a solution of diethyl ketone (0.03 ml) in dry THF (0.3 ml)). After stirring at the same temperature for 30 min, the reaction mixture was kept at room temperature for 2 h, before quenching with wet THF, partitioning between ether and water, and standard work-un (chromatography: 1% h v:v ether in petroleum ether) to give the compound 550:

$^1$H-NMR: δ (CDCl$_3$)=6.45 (d,1H), 6.18 (dd,1H), 5.81 (d,1H), 5.71 (d,1H), 5.43 (dd,1H), 4.98 (m,1H), 4.93 (m,1H), 4.53 (m,1H), 4.21 (m,1H), 2.87 (d,1H), 2.54 (dd,1H), 2.30 (bd,1H), 2.20-1.10 (m,18H), 1.05 (d,3H), 1.00 (m,6H), 0.88 (s,9H), 0.86 (s,9H), 0.56 (s,3H), 0.05 (bs,12H) ppm.

Preparation 32: Compound 303

A solution of 24-diphenylphosphinoyl-1(S),3(R)-di-TBS-oxy-9,10-seco-chola-5(E),7(E),10(19),22(E)-tetra-ene (see Preparation 33) (2.4 g, 3.1 mmol) in DCM (5 ml) was briefly cooled on a dry-ice bath for the addition of liquid sulphur dioxide (10 ml). The mixture was stirred under reflux (dry-ice cold finger condenser) without further cooling for 30 min, after which the solvents were removed in vacuo and the product crystallised from ether to give the major isomer sulphur dioxide adduct of 24-diphenylphosphinoyl-1(S),3(R)-di-TBS-oxy-9,10-seco-chola-5(E),7(E),10(19),22(E)-tetra-ene:

$^1$H-NMR: δ (CDCl$_3$)=7.80-7.65 (m,4H), 7.55-7.40 (m,6H), 5.34 (m,2H), 4.60 (m,2H), 4.36 (m,1H), 4.18 (m,1H), 3.92 (m,1H), 3.58 (bd,1H), 3.04 (m,2H), 2.56 (m,1H), 2.14 (bd,1H), 2.05-1.00 (m,15H), 0.88 (d,3H), 0.87 (bs,18H), 0.55 (s,3H), 0.05 (bs,12H) ppm.

To a stirred solution, maintained at about 5° C., of this adduct (1.8 g, 2.1 mmol) in dry DCM (30 ml) was added dropwise boron trifluoride etherate (1.2 ml). After 16 h at 3-5° C., 5% aq. sodium hydrogen carbonate solution was added before diluting with ether and performing the standard work-up (chromatography: 25% v:v acetone in DCM) to give as the main product one isomer of the sulphur dioxide adduct of 24-diphenylphosphinoyl-3(R)-hydroxy-1(S)-TBS-oxy-9,10-seco-chola-5(E),7(E),10(19),22(E)-tetra-ene:

$^1$H-NMR: δ (CDCl$_3$)=7.75-7.67 (m,4H), 7.48-7.42 (m,6H), 5.34 (m,2H), 4.68 (m,2H), 4.36 (bt,1H), 4.21 (m,1H), 3.92 (bd,1H), 3.58 (bd,1H), 3.04 (m,2H), 2.57 (m,1H), 2.24 (bd,1H), 2.00-0.95 (m,16H), 0.89 (d,3H), 0.87 (s,9H), 0.54 (s,3H), 0.08 (s,3H), 0.07 (s,3H) ppm.

A stirred solution, maintained at about 5° C., of this alcohol (0.61 g, 0.84 mmol) in dry DCM (10 ml) was treated with the Dess-Martin periodinane (0.5 g). After 30 min 5% aq. sodium hydrogen carbonate solution and 10% aq. sodium thiosulphate solution were added and stirring continued for 10 min before dilution with ether and performing the standard work-up (chromatography: 25% v:v acetone in DCM) to give one isomer of the sulphur dioxide adduct of 24-diphenylphosphinoyl-3-oxo-1(S)-TBS-oxy-9,10-seco-chola-5(E),7(E),10(19),22(E)-tetra-ene. This ketone (0.53 g, 0.72 mmol) was dissolved in THF-methanol (2+5 ml) and treated with sodium borohydride (43 mg) while stirring on an ice bath. After the reduction was complete (15 min), the reaction mixture was partitioned between ethyl acetate and water. Standard work-up (without chromatography) gave the 3(S)-hydroxy compound in admixture with a small amount of the 3(R)-hydroxy compound already described. The product was heated under reflux in toluene (10 ml)/water (10 ml) containing suspended sodium hydrogen carbonate (1.2 g) for 1 h. After cooling, partitioning between ether and water followed by standard work-up (without chromatography) gave 24-diphenylphosphinoyl-3(S)-hydroxy-1(S)-TBS-oxy-9,10-seco-chola-5(E), 7(E),10(19),22(E)-tetra-ene in admixture with a small amount of the 3(R)-hydroxy compound. The product was submitted to the process of General Procedure 7 (without chromatography), using 9-acetyl-anthracene (0.02 g) and DCM to give the 5(Z)-isomer. To a stirred, ice-cooled solution of this product in dry DCM (10 ml) and 2,6-lutidine (0.2 ml) was added TBS triflate (0.3 ml), and after allowing to react for 1 h, the mixture was partitioned between water and ether, and worked up as standard (chromatography: 25% v:v acetone in DCM) to give 24-diphenylphosphinoyl-1(S),3(S)-Di-TBS-oxy-9,10-seco-chola-5(E),7(E),10(19),22(E)-tetra-ene:

$^1$H-NMR: δ (CDCl$_3$)=7.80-7.65 (m,4H), 7.50-7.40 (m,6H), 6.23 (d,1H), 5.94 (d,1H), 5.37 (bt,1H), 5.34 (m,2H), 4.91 (bt,1H), 3.93 (m,1H), 3.68 (m,1H), 3.05 (m,2H), 2.78 (dd,1H), 2.41 (bd,1H), 2.25-0.90 (m,15H), 0.93 (s,9H), 0.87 (s,9H), 0.86 (d,3H), 0.46 (s,3H), 0.10 (s,3H), 0.07 (s,3H), 0.06 (s,3H), 0.05 (s,3H) ppm. The lithio-derivative 303 was prepared as required from this precursor by adding dropwise n-butyl-lithium (1.6M in hexanes, 1 molar equiv.) to a stirred solution, maintained at about −70° C., in dry THF and keeping at the same temperature for 15 min.

Preparation 33: Compound 302

To a stirred solution of 1(S),3(R)-di-TBS-oxy-9,10-seco-chola-5(E),7(E),10(19),22(E)-tetra-ene-24-ol (1.17 g, 1.94 mmol) in dry THF (15 ml) at room temperature was added triphosgene (0.43 g) and then dropwise pyridine (0.5 ml). After 90 min at the same temperature, the mixture was partitioned between water and ether, and worked up as standard (chromatography: 1% v:v ether in petroleum ether) to give 24-chloro-1(S),3(R)-di-TBS-oxy-9,10-seco-chola-5(E),7(E),10(19),22(E)-tetra-ene:

$^{13}$C-NMR: δ (CDCl$_3$)=153.5, 142.8, 141.8, 135.4, 123.5, 121.5, 116.4, 106.4, 70.0, 67.0, 56.2, 55.7, 45.7, 45.5, 43.8, 40.2, 39.6, 36.4, 28.7, 27.4, 25.7, 25.6, 23.3, 22.0, 19.9, 18.1, 17.9, 12.1, −5.0, −5.1 ppm.

To a stirred solution, maintained at about −70° C., of this chloride (0.81 g) in dry THF (7 ml) was added dropwise a solution of lithium diphenylphosphide (0.4M in dry THF, 3.5 ml). A few drops of water were then added before warming to room temperature and concentration in vacuo, to give an oil. This was taken up in DCM (15 ml) and stirred vigorously with 5% hydrogen peroxide (aq., 12 ml) for 30 min. The mixture was partitioned between water and ether, and worked up as standard (chromatography: 66% v:v ethyl acetate in petroleum ether) to give 24-diphenylphosphinoyl-1(S),3(R)-di-TBS-oxy-9,10-seco-chola-5(E),7(E),10(19),22(E)-tetra-ene:

$^1$H-NMR: δ (CDCl$_3$)=7.8-7.6 (m,4H), 7.5-7.4 (m,6H), 6.42 (d,1H), 5.77 (d,1H), 5.45-5.25 (m,2H), 4.96 (bs,1H), 4.92 (bs,1H), 4.52 (m,1H), 4.20 (m,1H), 3.07 (d,1H), 3.02 (d,1H), 2.84 (bd,1H), 2.55 (dd,1H), 2.27 (bd,1H), 2.05-0.90 (m,14H), 0.88 (s,9H), 0.87 (d,3H), 0.86 (s,9H), 0.47 (s,3H), 0.05 (s,12H) ppm.

The lithio-derivative 302 was prepared as required from this precursor by adding dropwise n-butyl-lithium (1.6M in hexanes, 1 molar equiv.) to a stirred solution, maintained at about −70° C., in dry THF and keeping at the same temperature for 15 min.

Preparation 34: Compound 534

To a solution, maintained at about −70° C., of the lithio-derivative 302 (prepared from the precursor 24-diphenylphosphinoyl-1(S),3(R)-di-TBS-oxy-9,10-seco-chola-5(E),7(E),10(19),22(E)-tetra-ene (0.71 g, 0.88 mmol) and n-butyl-lithium (0.55 ml)) in dry THF (8 ml)) was added dropwise a solution of hexafluoro-acetone (1 ml of ca. 1M solution in dry THF). After stirring at the same temperature for 30 min, the reaction mixture was kept at room temperature for 4 h before quenching with wet THF, partitioning between ether and water, and standard work-up (chromatography: 5% v:v ether in petroleum ether) to give the compound 534:

$^{13}$C-NMR: δ (CDCl$_3$)=157.3, 153.5, 142.3, 142.2, 135.6, 121.5, 121.4, 121.3, 120.5, 116.6, 106.5, 70.0, 67.0, 56.0, 55.3, 46.0, 43.8, 40.9, 40.2, 36.4, 28.7, 27.4, 25.7, 25.6, 23.2, 22.1, 19.4, 18.1, 17.9, 12.1, −4.9, −5.0, −5.1, −5.1 ppm.

Preparation 35: Compound 205 [1→2]

A mixture of compound 101 (5.00 g, 8,7 mmol), 1-(triphenylphosphoranylidene)-2-propanone (8.32 g, 26,1 mmol), and toluene (100 ml) was stirred for 18 hours at 110° C. The reaction mixture was cooled to room temperature, filtered, and concentrated in vacuo. The residue was dissolved in pentane (75 ml), stirred for 45 minutes at room temperature, and filtered through Decalite filter aid. The filtrate was concentrated in vacuo and purified by chromatography (0-5% v:v ether in petroleum ether).

Compound 205: $^1$H-NMR: δ=6.66 (dd,1H,J=8.8 Hz and 16.1 Hz), 6.44 (d,1H), 6.00 (d,1H,J=16.1 Hz), 5.81 (d,1H), 4.98 (m,1H), 4.93 (m,1H), 4.53 (m,1H), 4.21 (m,1H), 2.88 (m,1H), 2.54 (dd,1H), 2.38-2.16 (m,2H), 2.22 (s,3H), 2.10-1.85 (m,3H), 1.82-1.18 (m,10H), 1.11 (d,3H), 0.89 (s,9H), 0.86 (s,9H), 0.57 (s,3H), 0.08-0.02 (m,12H).

General Procedure 7 (Preparations 101-126, 128) [a→b (B=CH$_2$)]

A solution of the 5E-Vitamin D intermediate of type a (0.1 mmol), a triplet-sensitizer (0.01 g), and triethylamine (0.05 ml) in a solvent (5 ml) in a Pyrex flask was irradiated with light from a high pressure ultraviolet lamp, type TQ180Z2 (Hanau) at about 20° C. for 30 minutes (the time was scaled-up proportionally according to the amount of intermediate a). The reaction mixture (after filtering when anthracene was used) was partially concentrated in vacuo and purified by chromatography to give the product intermediate of type b.

Preparation 101: Compound 519

Intermediate of type a: 501 (1.29 g, 2.06 mmol).
Sensitizer: Anthracene (0.65 g).
Solvent: DCM (100 ml).
Irradiation: A TQ718Z2 lamp was used for 35 min.
Compound 519: $^1$H-NMR: δ=6.23 (d, 1H), 6.13 (dd, 1H, J=11.1 Hz and 14.9 Hz), 6.00 (d, 1H), 5.75 (d, 1H, J=11.1 Hz), 5.40 (dd, 1H, J=8.8 Hz and 14.9 Hz), 5.17 (m, 1H), 4.85 (m, 1H), 4.36 (m, 1H), 4.18 (m, 1H), 2.82 (m, 1H), 2.44 (dd, 1H), 2.21 (dd, 1H), 2.11 (m, 1H), 1.74 (bs, 3H), 1.73 (bs, 3H), 2.03-1.14 (m, 13H), 1.04 (d, 3H), 0.87 (s, 18H), 0.55 (s, 3H), 0.05 (m, 12H) ppm.

Preparation 102: Compound 521

Intermediate of type a: 502 (63 mg).
Sensitizer: 9-acetyl-anthracene.
Solvent: DCM.
Compound 521: $^1$H-NMR in agreement with structure.

Preparation 103: Compound 523

Intermediate of type a: 503 (0.38 g).
Sensitizer: Anthracene (0.32 g).
Solvent: DCM.
Purification of compound 523 by chromatography (0.5% v:v, ether in petroleum ether).

Compound 523: $^1$H-NMR: δ=6.22 (d, J=11.2 Hz, 1H), 6.11 (dd, J=14.9 Hz, J=10.7 Hz, 1H), 6.00 (d, J=11.2 Hz, 1H), 5.76 (d, J=10.7 Hz; 1H), 5.41 (dd, J=9.6 Hz, J=14.9 Hz, 1H), 5.17 (m, 1H), 4.86 (m, 1H), 4.36 (m, 1H), 4.18 (m, 1H), 2.80 (m, 1H), 2.43 (dd, J=3.8 Hz, J=13.0 Hz, 1H), 2.20 (dd, J=7.5 Hz, J=13.0 Hz, 1H), 2.15-1.0 (m, 14H), 1.75 (bs, 3H), 1.72 (bs, 3H), 0.93 (d, J=6.5 Hz, 3H), 0.87 (s, 9H), 0.86 (s, 9H), 0.49 (s, 3H), 0.05 (bs, 12H) ppm.

Preparation 104: Compound 524

Intermediate of type a: 504 (61 mg).
Sensitizer: Anthracene (0.05 g).
Solvent: DCM.
Purification of compound 524 by chromatography (0-2% v:v, ether in petroleum ether).

Compound 524: $^1$H-NMR: δ=6.33 (bd, J=10.3 Hz, 1H), 6.22 (d, J=11.2 Hz, 1H), 6.11 (dd, J=10.3 Hz, J=15.3 Hz, 1H), 6.01 (d, J=11.2 Hz,1H), 5.55 (dd, J=15.3 Hz, J=8.8 Hz, 1H), 5.17 (bs, 1H), 4.86 (bs, 1H), 4.18 (m, 1H), 2.81 (m, 1H), 2.44 (m, 1H), 2.25-1.0 (m, 20H), 1.06 (d, J=6.8 Hz, 3H), 0.87 (s, 18H), 0.55 (s, 3H), 0.05 (bs, 12H) ppm.

Preparation 105: Compound 525

Intermediate of type a: 505 (0.24 g).
Sensitizer: Anthracene (0.23 g).
Solvent: DCM.
Purification of compound 525 by chromatography (0-2% v:v, ether in petroleum ether).

Compound 525: $^1$H-NMR: δ=6.35 (bd, J=10.3 Hz, 1H), 6.22 (bd, J=11.5 Hz, 1H), 6.08 (dd, J=10.3 Hz, J=15.4 Hz, 1H), 6.00 (d, J=11.5 Hz, 1H), 5.55 (dd, J=9.4 Hz, J=15.4 Hz, 1H), 5.17(bd, 1H), 4.86 (bd, 1H), 4.36 (m, 1H), 4.18 (m, 1H), 2.80 (bd, J=12.2 Hz, 1H), 2.43 (dd, J=3.6, J=13.0 Hz, 1H), 2.20 (dd, J=7.3 Hz, J=13.0 Hz, 1H), 2.15-1.0 (m, 18H), 0.97 (d, J=6.8 Hz, 3H), 0.87 (s, 9H), 0.87 (s, 9H), 0.50 (s, 3H), 0.05 (bs, 12H) ppm.

Preparation 106: Compound 526

Intermediate of type a: 506 (0.4 g).
Sensitizer: Anthracene (0.34 g).
Solvent: DCM.
Purification of compound 526 by chromatography (0.5% v:v, ether in petroleum ether).

Compound 526: $^1$H-NMR: δ=6.22 (d, J=11.2 Hz, 1H), 6.00 (d, J=11.2 Hz, 1H), 5.84 (dd, J=15 Hz, J=10.7 Hz, 1H), 5.65 (m, 1H), 5.34 (dd, J=15 Hz, J=8.7 Hz, 1H), 5.17 (bs, 1H), 4.85 (bs, 1H), 4.36 (m,1H), 4.18 (m, 1H), 2.69 (m, 5H), 2.44 (m, 1H), 2.25-1.10 (m, 17H), 1.03 (d, J=6.7 Hz, 3H), 0.87 (s, 18H), 0.54 (s, 3H), 0.05 (bs, 12H) ppm.

Preparation 107: Compound 527

Intermediate of type a: 507 (0.38 g).
Sensitizer: Anthracene (0.32 g).
Solvent: DCM.
Purification of compound 527 by chromatography (0.5% v:v, ether in petroleum ether).

Compound 527: $^{13}$C-NMR: δ=148.2, 142.3, 140.9, 137.5, 134.7, 123.5, 123.0, 120.9, 117.6, 110.9, 71.9, 67.3, 56.7, 56.0, 45.8, 45.7, 44.6, 40.6, 39.7, 31.0, 29.7, 28.7, 27.1, 25.7, 25.6, 23.2, 21.8, 21.3, 18.0, 17.9, 16.9, 12.0, −4.9, −5.0, −5.3 ppm.

Preparation 108: Compound 528

Intermediate of type a: 510 (0.15 g).
Sensitizer: 9-acetyl-anthracene (0.02 g).
Solvent: DCM.
Compound 528: $^1$H-NMR in agreement with structure.

Preparation 109: Compound 529

Intermediate of type a: 511 (24 mg, 0.04 mmol).
Sensitizer: 9-acetyl-anthracene.
Solvent: Toluene.
Compound 529: $^1$H-NMR in agreement with structure.

Preparation 110: Compound 530
  Intermediate of type a: 514 (125 mg, 0.2 mmol).
  Sensitizer: 9-acetyl-anthracene.
  Solvent: DCM.
  Compound 530: $^1$H-NMR in agreement with structure.
Preparation 111: Compound 531
  Intermediate of type a: 515 (17 mg).
  Sensitizer: Anthracene (0.01 g).
  Solvent: Toluene (2 ml).
  Compound 531: $^1$H-NMR in agreement with structure.
Preparation 112: Compound 532
  Intermediate of type a: 516 (90 mg).
  Sensitizer: 9-acetyl-anthracene.
  Solvent: DCM.
  Compound 532: $^1$H-NMR in agreement with structure.
Preparation 113: Compound 533
  Intermediate of type a: 517 (0.10 g, 0.16 mmol).
  Sensitizer: 9-acetyl-anthracene.
  Solvent: DCM.
  Compound 533: $^1$H-NMR: δ=6.23 (d, 1H), 6.03 (d,1H, J=15.6 Hz), 6.01 (d, 1H), 5.88 (dd, 1H, J=8.4 Hz and 15.6 Hz), 5.17 (m, 1H), 4.86 (m, 1H), 4.78 (m, 1H), 4.72 (m, 1H), 4.37 (m, 1H), 4.18 (m, 1H), 2.83 (m, 1H), 2.45 (dd,1H), 2.30-2.06 (m, 2H), 2.05-1.95 (m, 2H), 1.07 (d, 3H), 0.87 (s, 18H), 1.93-0.80 (m, 12H), 0.67 (m, 2H), 0.56 (s, 3H), 0.41 (m, 2H), 0.05 (m, 6H), 0.04 (m, 6H) ppm.
Preparation 114: Compound 520
  Intermediate of type a: 518 (57 mg).
  Sensitizer: Anthracene (0.05 g).
  Solvent: DCM.
  Purification of compound 520 by chromatography (0.5% v:v, ether in petroleum ether).
  Compound 520: $^1$H-NMR: δ=6.87 (d, J=9.9 Hz, 1H), 6.22 (d, J=11.2 Hz, 1H), 6.00 (d, J=11.2 Hz, 1H), 6.01 (dd, J=9.9 Hz, J=15.3 Hz, 1H), 5.81 (dd, J=15.3 Hz, J=9.5 Hz, 1H), 5.17 (bm, 1H), 4.85 (bm, 1H), 4.36 (m, 1H), 4.19 (m, 1H), 2.81 (bm, 1H), 2.44 (dd, 1H), 2.2-1.0 (m, 15H), 0.95 (d, J=6.6 Hz, 3H), 0.87 (bs, 18H), 0.50 (s, 3H), 0.05 (bs, 12H) ppm.
Preparation 115: Compound 1002
  Intermediate of type a: 1001 (104 mg, 0.17 mmol).
  Sensitizer: 9-acetylanthracene.
  Solvent: tert-butyl methyl ether.
  Compound 1002: $^1$H-NMR in agreement with structure.
Preparation 116: Compound 1004
  Intermediate of type a: 1003 (41 mg).
  Sensitizer: 9-acetylanthracene (10 mg).
  Solvent: Toluene (4 ml).
  Compound 1004: $^1$H-NMR: δ=6.23 (d, 1H), 6.00 (d, 1H), 5.17 (m, 1H), 4.85 (m, 1H), 4.37 (m, 1H), 4.18 (m, 1H), 2.82 (m, 1H), 2.44 (dd,1H), 1.52 (s, 6H), 1.17 (d, 3H), 0.87 (s, 18H), 2.38-0.80 (m, 16H), 0.56 (s, 3H), 0.05 (s, 6H), 0.04 (s, 6H) ppm.
Preparation 117: Compound 1006
  Intermediate of type a: 1005 (70 mg, 0.1 mmol).
  Sensitizer: Anthracene (80 mg).
  Solvent: DCM.
  Compound 1006: $^{13}$C-NMR: δ=148.1, 140.0, 135.2, 122.8, 118.0, 111.0, 85.1, 78.4, 72.5, 71.7, 69.3, 67.3, 64.8, 55.7, 55.5, 45.8, 45.5, 44.6, 39.5, 34.1, 28.6, 28.3, 26.4, 25.6, 25.6, 23.0, 21.9, 20.7, 18.0, 17.9, 12.2, 8.3, −4.9, −5.0, −5.3 ppm.
Preparation 118: Compound 1008
  Intermediate of type a: 1007 (68 mg, 0.1 mmol)
  Sensitizer: 9-acetylanthracene
  Solvent: DCM
  Compound 1008: $^1$H-NMR: δ=6.23 (d,1H), 6.00 (d,1H), 5.17 (m, 1H), 4.85 (m, 1H), 4.37 (m, 1H), 4.18 (m, 1H), 2.83 (m, 1H), 2.44 (dd,1H), 1.17 (d, 3H), 1.03 (t, 6H), 0.87 (s, 18H), 2.38-0.80 (m, 20H), 0.56 (s, 3H), 0.05 (m, 6H), 0.04 (m, 6H) ppm.
Preparation 119: Compound 537
  Intermediate of type a: 536 (150 mg).
  Sensitizer: Anthracene (0.112 g).
  Solvent: DCM.
  Purification of compound 537 by chromatography (0-2% v:v, ether in petroleum ether).
  Compound 537: $^1$H-NMR in agreement with structure.
Preparation 120: Compound 539
  Intermediate of type a: 538 (76 mg).
  Sensitizer: Anthracene (60 mg).
  Solvent: DCM.
  Purification of compound 539 by chromatography (0-2% v:v, ether in petroleum ether).
  Compound 539: $^1$H-NMR: δ=6.34 (d,1H,J=10.3 Hz), 6.22 (d,1H), 6.09 (dd,1H,J=10.3 Hz and 14.9 Hz), 6.01 (d,1H), 5.69 (dd,1H,J=8.8 Hz and 14.9 Hz), 5.17 (m,1H), 4.85 (d,1H), 4.36 (m,1H), 4.18 (m,1H), 2.82 (m,1H), 2.44 (dd,1H), 2.25-2.10 (m,2H), 2.05-1.10 (m,13H), 1.06 (d,3H), 0.87 (s,9H), 0.87 (s,9H), 0.55 (s,3H), 0.07-0.03 (m,12H ppm.
Preparation 121: Compound 541
  Intermediate of type a: 540 (120 mg).
  Sensitizer: Anthracene (115 mg). Solvent: DCM.
  Purification of compound 541 by chromatography (0-2% v:v, ether in petroleum ether).
  Compound 541: $^1$H-NMR: δ=6.23 (d,1H), 6.00 (d,1H), 5.99 (d,1H, J=15.6 Hz), 5.33 (dd,1H,J=8.8 Hz and 15.6 Hz), 5.17 (m,1H), 4.85 (bd,1H), 4.36 (m,1H), 4.18 (m,1H), 2.87-2.60 (m,5H), 2.44 (dd,1H), 2.21 (dd,1H), 2.16-1.10 (m,16H), 1.55 (bs,3H), 1.04 (d,3H), 0.87 (bs,18H), 0.55 (s,3H), 0.07-0.03 (m,12H) ppm.
Preparation 122: Compound 543
  Intermediate of type a: 542 (300 mg).
  Sensitizer: Anthracene (200 mg).
  Solvent: DCM.
  Purification of compound 543 by chromatography (0-2% v:v, ether in petroleum ether).
  Compound 543: $^1$H-NMR: δ=6.23 (d,1H), 6.01 (d,1H), 6.01 (dd,1H,J=11.1 Hz and 14.9 Hz), 5.86 (m,1H), 5.36 (dd, 1H,J=8.8 Hz and 14.9 Hz), 5.16 (m,1H), 4.85 (d,1H), 4.36 (m,1H), 4.18 (m,1H), 2.82 (m,1H), 2.44 (dd,1H), 2.37-0.80 (m,23H), 1.04 (d,3H), 0.87 (s,18H), 0.55 (s,3H), 0.07-0.03 (m,12H) ppm.
Preparation 123: Compound 545
  Intermediate of type a: 544 (214 mg).
  Sensitizer: Anthracene (150 mg).
  Solvent: DCM.
  Purification of compound 543 by chromatography (0-2% v:v, ether in petroleum ether).
  Compound 545: $^1$H-NMR: δ=6.23 (d,1H), 6.19 (dd,1H, J=10.7 Hz and 14.9 Hz), 6.00 (d,1H), 5.69 (d,1H, J=10.7 Hz), 5.43 (dd,1H,J=8.4 Hz and 14.9 Hz), 5.17 (m,1H), 4.85 (d,1H), 4.36 (m,1H), 4.18 (m,1H), 2.81 (m,1H), 2.44 (dd,1H), 2.32-0.80 (m,25H), 1.04 (d,3H), 0.87 (s,18H), 0.54 (s,3H), 0.07-0.03 (m,12H) ppm.
Preparation 124: Compound 547
  Intermediate of type a: 546 (217 mg).
  Sensitizer: Anthracene (214 mg).
  Solvent: DCM.
  Purification by chromatography (0-2% v:v, ether in petroleum ether) to give 1(S),3(R)-bis(tert-butyldimethylsilyloxy)-20(R)-cyclopropylidenemethyl-9,10-seco-pregna-5 (Z),7(E),10(19)-triene (compound 547).
  Compound 547: $^1$H-NMR: δ=6.22 (d,1H), 6.00 (d,1H), 5.62 (m,1H), 5.17 (m,1H), 4.86 (bd,1H), 4.36 (m,1H), 4.18

(m,1H), 2.79 (m,1H), 2.44 (dd,1H), 2.28 (m,1H), 2.20 (dd, 1H), 2.02-0.80 (m,17H), 0.96 (d,3H), 0.87 (s,9H), 0.87 (s,9H), 0.45 (s,3H), 0.09-0.02 (m,12H) ppm.

Preparation 125: Compound 549

Intermediate of type a: 546 (175 mg).
Sensitizer: Anthracene (157 mg).
Solvent: DCM.
Purification by chromatography (0-2% v:v, ether in petroleum ether) to give 1(S),3(R)-bis(tert-butyldimethylsilyloxy)-20(S)-cyclopropylidenemethyl-9,10-seco-pregna-5 (Z),7(E),10(19)-triene (compound 549).

Compound 549: $^1$H-NMR: δ=6.23 (d,1H), 6.01 (d,1H), 5.61 (m,1H), 5.17 (m,1H), 4.86 (bd,1H), 4.37 (m,2H), 4.19 (m,1H), 2.82 (m,1H), 2.44 (dd,1H), 2.32 (m,1H), 2.21 (dd, 1H), 2.06-0.80 (m,17H), 1.07 (d,3H), 0.87 (s,9H), 0.87 (s,9H), 0.56 (s,3H), 0.07-0.03 (m,12H) ppm.

Preparation 126: Compound 551

Intermediate of type a: 550 (0.07 g).
Sensitizer: 9-acetyl-anthracene (0.01 g).
Solvent: DCM (7 ml).
Compound 551: $^1$H-NMR (CDCl$_3$): δ=6.22 (d,1H), 6.17 (dd,1H), 6.00 (d,1H), 5.70 (d,1H), 5.43 (dd,1H), 5.16 (bd, 1H), 4.85 (bd,1H), 4.36 (m,1H), 4.18 (m,1H), 2.79 (dd,1H), 2.43 (dd,1H), 2.25-1.15 (m,19H), 1.04 (d,3H), 1.00 (m,6H), 0.86 (bs,18H), 0.54 (s,3H), 0.05 (bs,12H) ppm.

Preparation 127: Compound 552

To a solution, maintained at about −70° C., of the lithio-derivative 303 (prepared from the precursor 24-diphenylphosphinoyl-1(S),3(S)-Di-TBS-oxy-9,10-seco-chola-5 (E),7(E),10(19),22(E)-tetra-ene (0.13 g, 0.16 mmol) and n-butyl-lithium (0.1 ml)) in dry THF (2 ml)) was added dropwise a solution of diethyl ketone (0.025 ml) in dry THF (0.25 ml)). After stirring at the same temperature for 30 min, the reaction mixture was kept at room temperature for 2 h and then at 40° C. for 1 h, before quenching with wet THF, partitioning between ether and water, and standard work-up (chromatography: 20% v:v toluene in petroleum ether) to give the compound 552:

$^1$H-NMR in agreement with structure.

Preparation 128: Compound 535

Intermediate of type a: 534 (0.09 g).
Sensitizer: 9-acetyl-anthracene (0.01 g).
Solvent: DCM (7 ml).
535: $^1$H-NMR (CDCl$_3$): δ=6.96 (d,1H), 6.43 (t,1H), 6.22 (d,1H), 6.19 (dd,1H), 6.01 (d,1H), 5.15 (m,1H), 4.84 (d,1H), 4.36 (m,1H), 4.18 (m,1H), 2.82 (d,1H), 2.41 (dd,1H), 2.40-2.15 (m,2H), 2.0-1.15 (m,13H), 1.15 (d,3H), 0.87 (s,9H), 0.86 (s,9H), 0.57 (s,3H), 0.05 (s,6H), 0.04 (s,6H) ppm.

General Procedure 8 (Examples 4, 14-18, 23, 25-27, 29, and 36)

To a mixture, maintained at about 25° C., of an ethyl acetate solution (about 0.3 ml) of the appropriate silyl-protected intermediate (ca. 0.1 mmol) in acetonitrile (4 ml) was added (via plastic pipette) 40% aqueous hydrofluoric acid (0.5 ml, ca. 10 mmol). After vigorous stirring at the same temperature for 1 h, the reaction mixture was partitioned between ethyl acetate and 3N sodium hydroxide (to alkaline reaction to pH paper) solution before standard work-up to give the compound I.

General Procedure 9 (Examples 1-3, 5-13, 28, 30-33)

To a solution of the appropriate silyl-protected intermediate (0.1 mmol) in THF (4 ml) was added solid TBA-fluoride trihydrate (0.13 g, ca. 0.4 mmol), and the solution was heated at 60° C. for one hour. After cooling (and partial concentration in vacuo when the volume of THF in a scaled-up procedure exceeded 30 ml), 0.2 M aqueous sodium hydrogen carbonate solution and ethyl acetate were added. Standard work-up gave the compound I.

Example 1

1(S),3(R)-Dihydroxy-9,10-secocholesta-5(Z),7(E),10 (19),22(E),24-penta-ene (Compound 1)

A solution of 519 (2.1 g, 3.36 mmol) and tetra-n-butylammonium fluoride trihydrate (5.42 g, 17.2 mmol) in tetrahydrofuran (70 ml) was heated at 60° C. in an argon atmosphere for 60 minutes. After cooling and concentration in vacuo, the reaction mixture was partitioned between ethyl acetate and aqueous sodium bicarbonate. The organic phase was washed with water and brine, dried and concentrated. The residue was purified by chromatography (50% ethyl acetate in petroleum ether). Fractions containing the title compound were concentrated in vacuo to yield an oil which gave colourless crystals from methyl formate. Compound 1: $^{13}$C-NMR: δ=147.7, 143.1, 138.2, 132.9, 132.8, 125.3, 125.0, 124.3, 117.1, 111.8, 70.8, 66.9, 56.4, 45.9, 45.3, 42.9, 40.5, 40.4, 29.1, 27.8, 25.9, 23.6, 22.3, 20.8, 18.2, 12.3 ppm.

Example 2

1(S),3(R)-Dihydroxy-9,10-secocholesta-5(Z),7(E),10 (19),22(Z),24-penta-ene (Compound 2)

Silyl-protected intermediate: 521 (32 mg, 0.05 mmol).
Compound 2: $^{13}$C-NMR: δ=147.7, 143.1, 136.0, 134.8, 132.9, 125.0, 121.9, 120.6, 117.1, 111.7, 70.8, 66.9, 56.6, 56.4, 45.9, 45.3, 42.9, 40.5, 34.7, 29.1, 27.4, 26.4, 23.6, 22.3, 20.8, 18.1, 12.4 ppm.

Example 3

1(S),3(R)-Dihydroxy-9,10-seco-20(S)-cholesta-5(Z), 7(E),10(19), 22(E),24-penta-ene (Compound 3)

Silyl-protected intermediate: 523 (135 mg, 0.22 mmol).
Purification of compound 3 by chromatography (40% v:v, ethyl acetate in petroleum ether).
Compound 3: $^{13}$C-NMR: δ=147.7, 143.4, 138.6, 132.8, 132.5, 125.3, 125.0, 124.3, 116.9, 111.8, 70.9, 66.9, 56.9, 56.2, 46.0, 45.3, 42.9, 40.9, 39.7, 29.1, 27.3, 25.9, 23.5, 22.1, 21.5, 18.3, 12.2 ppm.

Example 4

1(S),3(R)-Dihydroxy-9,10-seco-26,27-cyclo-cholesta-5(Z),7(E),10(19),22(E),24-penta-ene (Compound 4)

Silyl-protected intermediate: 524 (36 mg).
Purification of compound 4 by chromatography (50% v:v, ethyl acetate in petroleum ether).
Compound 4: $^1$H-NMR: δ=6.37 (d, J=11 Hz, 1H), 6.34 (bd, J=10 Hz, 1H), 6.11 (dd, J=10 Hz, J=15 Hz, 1H), 6.01 (d, J=11 Hz, 1H), 5.56 (dd, J=9 Hz, J=15 Hz, 1H), 5.32 (bs, 1H), 5.00 (bs, 1H), 4.43 (m, 1H), 4.23 (m, 1H), 2.83 (dd, J=4 Hz, J=11

Hz, 1H), 2.59 (dd, J=4 Hz, J=13 Hz, 1H), 2.31 (dd, J=6 Hz, J=13 Hz, 1H), 2.2-1.2 (m, 16H), 1.10 (m, 4H), 1.07 (d, J=7 Hz, 3H), 0.58 (s, 3H) ppm.

Example 5

1(S),3(R)-Dihydroxy-9,10-seco-26,27-cyclo-20(S)-cholesta-5(Z),7(E),10(19),22(E),24-penta-ene (Compound 5)

Silyl-protected intermediate: 525 (165 mg, 0.26 mmol).
Purification of compound 5 by chromatography (50% v:v, ethyl acetate in petroleum ether).
Compound 5: $^{13}$C-NMR: δ=147.7, 143.2, 139.5, 132.9, 127.1, 125.0, 123.9, 119.1, 117.0, 111.8, 70.8, 66.8, 56.9, 56.2, 46.0, 45.3, 42.9, 40.7, 39.8, 29.1, 27.3, 23.5, 22.1, 21.3, 12.3, 2.4, 2.2 ppm.

Example 6

1(S),3(R)-Dihydroxy-9,10-seco-26,27-methano-cholesta-5(Z),7(E),10(19),22(E),24-penta-ene (Compound 6)

Silyl-protected intermediate: 526 (348 mg, 0.55 mmol).
Isolation from the crude product by direct crystallisation from methyl formate, omitting the chromatography step.
Compound 6: $^{13}$C-NMR: δ=147.6, 143.1, 142.8, 137.2, 133.0, 125.0, 123.9, 121.0, 117.1, 111.8, 70.8, 66.9, 56.4, 56.4, 45.9, 45.3, 42.9, 40.4, 40.4, 31.3, 29.9, 29.1, 27.8, 23.6, 22.2, 20.8, 17.2, 12.3 ppm.

Example 7

1(S),3(R)-Dihydroxy-9,10-seco-26,27-methano-20(S)-cholesta-5(Z),7(E),10(19),22(E),24-penta-ene (Compound 7)

Silyl-protected intermediate: 527 (150 mg, 0.23 mmol).
Purification of compound 7 by chromatography (40% v:v, ethyl acetate in petroleum ether).
Compound 7: $^{13}$C-NMR: δ=147.7, 143.3, 142.6, 137.6, 132.8, 125.0, 123.8, 121.1, 116.9, 111.8, 70.9, 66.9, 56.9, 56.2, 46.0, 45.3, 42.9, 40.8, 39.8, 31.3, 29.9, 29.1, 27.3, 23.5, 22.1, 21.5, 17.1, 12.2 ppm.

Example 8

1(S),3(R),26-Trihydroxy-9,10-secocholesta-5(Z),7(E),10(19),22(E),24(E)-penta-ene (Compound 9)

Silyl-protected intermediate: 528 (148 mg, 0.23 mmol).
Purification of compound 9 by crystallisation from methyl formate.
Compound 9: $^{1}$H-NMR: (in hexadeuterioacetone) δ=6.29 (d, 1H), 6.25 (dd, 1H, J=11.1 Hz and 15.1 Hz), 6.09 (d, 1H), 5.99 (d, 1H, J=11.1 Hz), 5.52 (dd, 1H, J=8.8 Hz and 15.1 Hz), 5.31 (m, 1H), 4.86 (m, 1H), 4.39 (m, 1H), 4.17 (m, 1H), 3.96 (d, 2H), 3.86 (d, OH), 3.68 (t, OH), 3.62 (d, OH), 2.87 (m, 1H), 2.50 (dd, 1H), 2.29 (dd, 1H), 2.20 (m, 1H), 1.72 (bs, 3H), 2.10-1.20 (m, 13H), 1.08 (d, 3H), 0.60 (s, 3H) ppm.

Example 9

1(S),3(R),26-Trihydroxy-9,10-seco-20(S)-cholesta-5(Z),7(E),10(19),22(E),24(E)-penta-ene (Compound 10)

Silyl-protected intermediate: 529 (0.126 g, 0.2 mmol)
Compound 10: $^{13}$C-NMR: δ=147.7, 143.2, 141.8, 134.5, 132.9, 125.5, 125.0, 123.4, 117.0, 111.8, 70.9, 68.7, 66.8, 56.8, 56.2, 46.0, 45.3, 42.9, 41.0, 39.8, 29.1, 27.2, 23.5, 22.1, 21.3, 14.2, 12.3 ppm.

Example 10

1(S),3(R),26-Trihydroxy-9,10-secocholesta-5(Z),7(E),10(19),22(E),24(Z)-penta-ene (Compound 11)

Silyl-protected intermediate: 530 (24 mg, 0.04 mmol).
Compound 11: $^{1}$H-NMR: δ=6.38 (d, 1H), 6.22 (dd, 1H, J=11.1 Hz and 14.9 Hz), 6.01 (d, 1H), 5.88 (d, 1H, J=11.1 Hz), 5.51 (dd, 1H, J=8.8 Hz and 14.9 Hz), 5.32 (m, 1H), 5.00 (m, 1H), 4.43 (m, 1H), 4.24 (s, 2H), 4.22 (m, 1H), 2.83 (m, 1H), 2.60 (dd, 1H), 2.31 (dd, 1H), 2.13 (m, 1H), 1.85 (bs, 3H), 1.05 (d, 3H), 2.08-0.80 (m, 16H), 0.56 (s, 3H) ppm.

Example 11

1(S),3(R),26-Trihydroxy-9,10-seco-20(S)-cholesta-5(Z),7(E),10(19),22(E),24(Z)-penta-ene (Compound 12)

Silyl-protected intermediate: 531 (17 mg, 0.03 mmol).
Compound 12: $^{1}$H-NMR: δ=6.37 (d, 1H), 6.20 (dd, 1H, J=11.1 Hz and 14.9 Hz), 6.01 (d, 1H), 5.89 (d, 1H, J=11.1 Hz), 5.52 (dd, 1H, J=9.5 Hz and 14.9 Hz), 5.33 (m, 1H), 5.00 (m, 1H), 4.43 (m, 1H), 4.24 (s, 2H), 4.22 (m, 1H), 2.81 (m, 1H), 2.60 (dd, 1H), 2.31 (dd, 1H), 1.86 (bs, 3H), 0.94 (d, 3H), 2.20-0.80 (m, 17H), 0.50 (s, 3H) ppm.

Example 12

1(S),3(R)-Dihydroxy-20(R)-(4-methyl-5-ethyl-5-hydroxy-1(E),3(E)-heptadienyl)-9,10-secopregna-5(Z),7(E),10(19)-triene (Compound 13)

Silyl-protected intermediate: 532 (90 mg, 0.13 mmol).
Compound 13: $^{13}$C-NMR: δ=147.7, 143.0, 140.2, 137.5, 133.0, 125.0, 124.6, 124.0, 117.1, 111.8, 78.4, 70.8, 66.8, 56.4, 56.4, 46.0, 45.3, 42.9, 40.5, 40.4, 31.8, 29.1, 27.7, 23.6, 22.3, 20.6, 14.2, 13.5, 12.3, 7.7 ppm.

Example 13

1(S),3(R)-Dihydroxy-20(R)-(3-cyclopropyl-1(E),3-butadienyl)-9,10-secopregna-5(Z),7(E),10(19)-triene (Compound 14)

Silyl-protected intermediate: 533 (0.10 mg, 0.16 mmol).
Purification of compound 14 by crystallisation from methyl formate.
Compound 14: $^{13}$C-NMR: δ=147.8, 147.7, 143.1, 137.0, 133.0, 129.9, 125.0, 117.1, 111.8, 110.5, 70.8, 66.9, 56.5, 56.4, 46.0, 45.3, 42.9, 40.4, 40.3, 29.1, 27.6, 23.6, 22.2, 20.6, 12.8, 12.3, 5.5 ppm.

Example 14

1(S),3(R)-Dihydroxy-9,10-secocholesta-5(Z),7(E),10(19),24-tetra-ene-22-yne (Compound 15)

Silyl-protected intermediate: 1002 (100 mg, 0.16 mmol).
Purification of compound 15 by chromatography (50% v:v, ethyl acetate in petroleum ether).

Compound 15: $^{13}$C-NMR: δ=147.4, 146.1, 142.6, 132.9, 124.7, 117.0, 111.6, 105.4, 96.4, 78.9, 70.6, 66.6, 56.1, 55.8, 45.6, 45.1, 42.7, 39.5, 28.8, 28.3, 26.3, 24.4, 23.2, 22.1, 21.6, 20.5, 12.3 ppm.

Example 15

1(S),3(R)-Dihydroxy-20(R)-(5-methyl-5-hydroxy-1, 3-hexadiynyl)-9,10-secopregna-5(Z),7(E),10(19)-triene (Compound 16)

Silyl-protected intermediate: 1004 (41 mg, 0.06 mmol).
Compound 16: $^{13}$C-NMR: δ=147.7, 142.7, 133.2, 124.9, 117.1, 111.8, 85.8, 80.6, 70.8, 67.4, 66.8, 65.6, 65.4, 55.9, 55.6, 45.9, 45.2, 42.9, 39.3, 31.2, 29.1, 28.2, 27.3, 23.5, 21.9, 20.5, 12.4 ppm.

Example 16

1(S),3(R)-Dihydroxy-20(S)-(5-ethyl-5-hydroxy-1,3-heptadiynyl)-9,10-secopregna-5(Z),7(E),10(19)-triene (Compound 17)

Silyl-protected intermediate: 1006 (66 mg, 0.1 mmol)
Compound 17: $^{13}$C-NMR: δ=147.6, 142.4, 133.4, 124.8, 117.4, 111.9, 85.1, 78.8, 72.7, 70.9, 69.4, 66.9, 65.3, 55.9, 55.8, 45.9, 45.3, 42.9, 39.6, 34.3, 29.0, 28.4, 26.3, 23.3, 22.2, 21.0, 12.5, 8.5 ppm.

Example 17

1(S),3(R)-Dihydroxy-20(R)-(5-ethyl-5-hydroxy-1,3-heptadiynyl)-9,10-secopregna-5(Z),7(E),10(19)-triene (Compound 18)

Silyl-protected intermediate: 1008 (69 mg, 0.1 mmol)
Compound 18: $^{13}$C-NMR: δ=147.7, 142.7, 133.2, 124.9, 117.1, 111.8, 85.2, 79.0, 72.7, 70.8, 69.4, 66.9, 65.6, 55.9, 55.6, 45.9, 45.3, 42.9, 39.3, 34.3, 29.1, 28.2, 27.3, 23.5, 22.0, 20.4, 12.4, 8.5 ppm.

Example 18

1(S),3(R)-Dihydroxy-20(S)-(4,4-dibromo-1,3-buta-dien-1yl)-9,10-seco-pregna-5(Z),7(E),10(19)-triene (Compound 8)

Silyl-protected intermediate: 520 (75 mg, 0.1 mmol)
Purification of compound 8 by chromatography (50% v:v, ethyl acetate in petroleum ether).
Compound 8: $^{13}$C-NMR: δ=147.4, 145.7, 142.6, 137.0, 132.9, 124.7, 124.7, 116.9, 111.6, 88.1, 70.6, 66.6, 56.4, 55.9, 45.7, 45.0, 42.7, 40.7, 39.5, 28.8, 26.9, 23.2, 21.8, 20.5, 12.1 ppm.

Example 19

1(S)-Fluoro-3(R)-hydroxy-9,10-secocholesta-5(Z),7 (E),10(19),22(E),24-penta-ene (Compound 21)

By general procedure 8 (but prolonging the reaction time to 5 h) compound 522 (0.8 g, 2.1 mmol) was desilylated to the corresponding alcohol, 8-beta-hydroxy-desAB-cholesta-22 (E),24-diene. A stirred solution, maintained at about 5° C., of this alcohol (0.39 g, 1.5 mmol) in dry DCM (10 ml) was treated with the Dess-Martin periodinane (0.7 g). After 30 min 5% aq. sodium hydrogen carbonate solution and 10% aq. sodium thiosulphate solution were added and stirring continued for 10 min before dilution with ether and performing the standard work-up to give the corresponding ketone, 8-oxo-desAB-cholesta-22(E),24-diene. This ketone (67 mg, 0.25 mmol) was slowly added in THF (3 ml) to a solution, maintained at about –70° C., of the lithio-derivative (generated in situ with 1 eq. n-BuLi) of phosphine oxide II (A=F, B=CH$_2$) (0.5 mmol) in dry THF (4 ml). After stirring at the same temperature for 2 h and warming to room temperature, the mixture was quenched with wet ether and worked up as standard (chromatography: 2% v:v ether in petroleum ether) to give the TBS derivative if compound 21. This was desilylated using general procedure 9 to give Compound 21.

Compound 21: $^1$H-NMR in agreement with structure.

Example 20

1(S),3(R)-Dihydroxy-19-nor-9,10-secocholesta-5,7 (E),22(E),24-tetra-ene (Compound 22)

By general procedure 8 (but prolonging the reaction time to 5 h) compound 522 (0.8 g, 2.1 mmol) was desilylated to the corresponding alcohol, 8-beta-hydroxy-desAB-cholesta-22 (E),24-diene. A stirred solution, maintained at about 5° C., of this alcohol (0.39 g, 1.5 mmol) in dry DCM (10 ml) was treated with the Dess-Martin periodinane (0.7 g). After 30 min 5% aq. sodium hydrogen carbonate solution and 10% aq. sodium thiosulphate solution were added and stirring continued for 10 min before dilution with ether and performing the standard work-up to give the corresponding ketone, 8-oxo-desAB-cholesta-22(E),24-diene. This ketone (67 mg, 0.25 mmol) was slowly added in THF (3 ml) to a solution, maintained at about –70° C., of the lithio-derivative (generated in situ with 1 eq. n-BuLi) of phosphine oxide II (A=O-TBS, B=H$_2$) (0.5 mmol) in dry THF (4 ml). After stirring at the same temperature for 2 h and warming to room temperature, the mixture was quenched with wet ether and worked up as standard (chromatography: 2% v:v ether in petroleum ether) to give the di-TBS derivative if compound 22. This was desilylated using general procedure 9 to give Compound 22.

Compound 22: $^1$H-NMR in agreement with structure.

Example 21

1(S),3(S)-Dihydroxy-9,10-secocholesta-5(Z),7(E),10 (19),22(E),24-penta-ene (Compound 23)

This compound was prepared analogously to Compound 29, using the intermediate of type 5 that was obtained analogously to Compound 552 by substituting acetone for the diethyl ketone.

Compound 23: $^1$H-NMR in agreement with structure.

Example 22

1(S),3(R)-Dihydroxy-9,10-secocholesta-5(Z),7(E),10 (19),16,22(E),24-hexa-ene (Compound 24)

This compound was prepared analogously to Compound 1(Example 1), but starting the sequence (of Preparations 1 and 101) using the intermediate of type 2a that was prepared from 104 analogously to the described preparation of 202 from 101 in WO9100855.

Compound 24: $^1$H-NMR in agreement with structure.

Example 23

1(S),3(R)-Dihydroxy-26,26,26,27,27,27-hexafluoro-9,10-secocholesta-5(Z),7(E),10(19),22(E),24-penta-ene (Compound 25)

Silyl-protected intermediate: 535 (55 mg).
Chromatography: 50% v:v ethyl acetate in petroleum ether.

Compound 25: $^1$H-NMR (CDCl$_3$): δ=6.96 (d,1H), 6.43 (t,1H), 6.35 (d,1H), 6.18 (dd,1H), 6.01 (d,1H), 5.31 (bs,1H), 4.98 (bs,1H), 4.41 (m,1H), 4.22 (m,1H), 2.80 (dd,1H), 2.57 (dd,1H), 2.30 (m,2H), 2.05-1.20 (m,8H), 1.10 (d,3H), 0.58 (s,3H) ppm.

Example 24

Capsules containing Compound 1

Compound 1 was dissolved in arachis oil to a final concentration of 10 µg of Compound 1/ml oil. 10 Parts by weight of gelatine, 5 parts by weight glycerine, 0.08 parts by weight potassium sorbate, and 14 parts by weight distilled water were mixed together with heating and formed into soft gelatine capsules. These were then filled each with 100 µl of Compound 1 in oil solution, such that each capsule contained 1 µg of Compound 1.

Example 25

1(S),3(R)-Dihydroxy-20(R)-(4,4-dibromo-1,3-buta-dien-1-yl)-9,10-seco-pregna-5(Z),7(E),10(19)-triene (Compound 27)

Silyl-protected intermediate: 537 (101 mg, 0.13 mmol).
Purification of compound 27 by chromatography (50% v:v, ethyl acetate in petroleum ether).

Compound 27: $^{13}$C-NMR: δ=147.7, 145.3, 142.7, 137.3, 133.2, 125.0, 124.9, 117.3, 111.8, 88.3, 70.8, 66.9, 56.2, 55.8, 46.0, 45.3, 42.9, 40.6, 40.3, 29.0, 27.6, 23.5, 22.3, 20.0, 12.3 ppm.

Example 26

1(S),3(R)-Dihydroxy-26,27-dimethyl-9,10-secocholesta-5(Z),7(E),10(19),22(E),24-penta-ene (Compound 28)

Silyl-protected intermediate: 551 (70 mg).
Purification of compound 28 by chromatography: 50% v:v ethyl acetate in petroleum ether Compound 28: $^{13}$C-NMR (CDCl$_3$): δ=147.4, 143.9, 142.9, 138.4, 132.7, 124.8, 123.9, 122.7, 116.9, 111.6, 70.6, 66.7, 56.2, 56.2, 45.7, 45.1, 42.7, 40.3, 40.2, 29.3, 28.9, 27.6, 23.6, 23.4, 22.1, 20.6, 13.2, 12.4, 12.1 ppm.

Example 27

1(S),3(S)-Dihydroxy-26,27-dimethyl-9,10-secocholesta-5(Z),7(E),10(19),22(E),24-penta-ene (Compound 29)

Silyl-protected intermediate: 552 (25 mg).
Purification of compound 30 by chromatography: 50% v:v ethyl acetate in petroleum ether.

Compound 29: $^1$H-NMR: δ=6.42 (d,1H), 6.17 (dd,1H), 6.00 (d,1H), 5.70 (d,1H), 5.43 (dd,1H), 5.28 (bd,1H), 4.98 (d,1H), 4.29 (m,1H), 4.03 (m,1H), 2.84 (dd,1H), 2.64 (bd,1H), 2.55 (dd,1H), 2.43 (dd,1H), 2.20-1.15 (m,19H), 1.04 (d,3H), 1.00 (m,6H), 0.56 (s,3H) ppm.

Example 28

1(S),3(R)-Dihydroxy-24-methyl-26,27-methano-9,10-secocholesta-5(Z),7(E),10(19),22(E),24-penta-ene (Compound 30)

Silyl-protected intermediate: 541 (47 mg, 0.072 mmol).
Purification of compound 30 by chromatography (50% v:v, ethyl acetate in petroleum ether).

Compound 30: $^1$H-NMR: δ=6.38 (d,1H), 6.01 (d,1H), 5.99 (d,1H,J=15.7 Hz), 5.33 (m,1H), 5.32 (m,1H), 5.00 (m,1H), 4.43 (m,1H), 4.23 (m,1H), 2.83 (dd,1H), 2.79-2.65 (m,4H), 2.60 (dd,1H), 2.31 (dd,1H), 2.22-1.16 (m,18H), 1.56 (bs,3H), 1.05 (d,3H), 0.57 (s,3H) ppm.

Example 29

1(S),3(R)-Dihydroxy-20(R)-(4,4-dichloro-1,3-buta-dien-1-yl)-9,10-seco-pregna-5(Z),7(E),10(19)-triene (Compound 31)

Silyl-protected intermediate: 539 (70 mg, 0.10 mmol).
Purification of compound 31 by chromatography (50% v:v, ethyl acetate in petroleum ether).

Compound 31: $^{13}$C-NMR: δ=147.7, 144.6, 142.6, 133.2, 129.2, 124.9, 122.4, 118.9, 117.3, 111.8, 70.8, 66.9, 56.3, 55.9, 46.0, 45.3, 42.9, 40.6, 40.3, 29.0, 27.6, 23.5, 22.3, 20.2, 12.3 ppm.

Example 30

1(S),3(R)-Dihydroxy-26,27-ethano-9,10-secocholesta-5(Z),7(E),10(19),22(E),24-penta-ene (Compound 32)

Silyl-protected intermediate: 543 (300 mg, 0.46 mmol).
Purification of compound 32 by chromatography (50% v:v, ethyl acetate in petroleum ether).

Compound 32: $^{13}$C-NMR: δ=147.6, 145.1, 143.1, 137.6, 132.9, 125.7, 125.0, 120.4, 117.1, 111.8, 70.8, 66.8, 56.4, 45.9, 45.2, 42.8, 40.5, 40.4, 33.9, 29.3, 29.1, 27.8, 26.4, 26.3, 23.6, 22.2, 20.8, 12.3 ppm.

Example 31

1(S),3(R)-Dihydroxy-26,27-propano-9,10-secocholesta-5(Z),7(E),10(19),22(E),24-penta-ene (Compound 33)

Silyl-protected intermediate: 545 (200 mg, 0.30 mmol).
Purification of compound 22 by chromatography (50% v:v, ethyl acetate in petroleum ether).

Compound 33: $^{13}$C-NMR: δ=147.6, 143.1, 140.9, 138.5, 132.9, 125.0, 123.6, 122.1, 117.1, 111.8, 70.8, 66.9, 56.5, 56.4, 46.0, 45.3, 42.9, 40.4, 37.2, 29.2, 29.1, 28.4, 27.8, 27.7, 26.9, 23.6, 22.3, 20.7, 12.3 ppm.

Example 32

1(S),3(R)-Dihydroxy-20(S)-cyclopropylidenem-ethyl-9,10-seco-pregna-5(Z),7(E),10(19)-triene (Compound 34)

Silyl-protected intermediate: 547 (143 mg, 0.24 mmol).
Purification of compound 34 by chromatography (50% v:v, ethyl acetate in petroleum ether).
Compound 34: $^{13}$C-NMR: δ=147.7, 143.4, 132.8, 125.1, 125.0, 118.0, 116.9, 111.8, 70.9, 66.9, 56.9, 56.1, 46.0, 45.3, 42.9, 39.9, 39.8, 29.2, 27.3, 23.6, 22.1, 20.9, 12.4, 2.1, 1.9 mmp.

Example 33

1(S),3(R)-Dihydroxy-20(R)-cyclopropylidenem-ethyl-9,10-seco-pregna-5(Z),7(E),10(19)-triene (Compound 35)

Silyl-protected intermediate: 549 (111 mg, 0.18 mmol).
Purification of compound 35 by chromatography (50% v:v, ethyl acetate in petroleum ether).
Compound 35: $^{13}$C-NMR: δ=147.7, 143.2, 132.9, 125.0, 124.5, 118.5, 117.0, 111.7, 70.8, 66.9, 56.8, 56.4, 45.9, 45.3, 42.9, 40.4, 39.7, 29.1, 27.5, 23.6, 22.3, 20.5, 12.2, 2.3, 1.9

Example 36

20-Epi-1(S),3(R)-dihydroxy-26,26,26,27,27,27-hexafluoro-9,10-secocholesta-5(Z),7(E),10(19),22(E),24-penta-ene (Compound 36)

This compound was prepared analogously to Compound 25 (Example 23), but starting the sequence (of Preparations 34 and 128) with 20-epi-1(S),3(R)-di-TBS-oxy-9,10-seco-chola-5(E),7(E),10(19),22(E)-tetra-ene-24-ol.
Compound 36: $^{1}$H-NMR in agreement with structure.

The invention claimed is:
1. A compound according to formula I

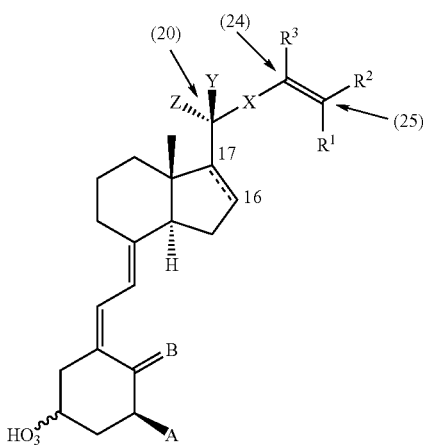

in which formula
R1 and R2, which are the same, represent halogen, ($C_1$-$C_6$) hydrocarbyl, optionally substituted with one or more fluorine atoms,
or, together with the carbon atom to which they are both attached, R1 and R2 form a ($C_3$-$C_6$) carbocyclic ring;
R3 represents hydrogen or methyl;
X represents (E)-ethenylene or (Z)-ethenylene;
Y and Z independently represent hydrogen or methyl;
the bond between C#16 and C#17 is depicted with a dotted line to illustrate that said bond is a single bond, in which case the projection of the ring substituent is beta;
A represents hydroxyl;
B represents $CH_2$;
the configuration in the 3-position corresponds to the same configuration as in natural vitamin $D_3$ (normal), or the configuration in the 3-position is opposite to natural vitamin $D_3$ (epi);
and in vivo hydrolysable esters and stereo isomeric forms thereof.

2. A compound according to claim 1 wherein R1 and R2 when taken separately, independently represent bromo, chloro, methyl, ethyl, trifluoromethyl, 1-propyl, 2-propyl, cyclopropyl, 2-methyl-2-propyl, or 3-pentyl.

3. A compound according to claim 1 wherein R1 and R2 are the same and both represent methyl, ethyl, bromo, or trifluoromethyl.

4. A compound according to claim 1 wherein R1 and R2 when taken together with the carbon atom to which they are both attached to form a $C_3$ carbocyclic ring or a $C_4$ carbocyclic ring.

5. A compound according to claim 4 wherein R1 and R2 when taken together are ethylene or tri-methylene, such as R1 and R2 when taken together with the carbon atom to which they are both attached to form a $C_3$ carbocyclic ring or a $C_4$ carbocyclic ring.

6. A compound according to claim 1 wherein R1 represents —$CMe_3$.

7. A compound according to claim 1 wherein the configuration in the 3-position corresponds to the configuration of natural vitamin $D_3$ (normal).

8. A compound according to claim 1 wherein the configuration in the 3-position corresponds to the opposite configuration to that of natural vitamin $D_3$ (epi).

9. A compound according to claim 1 selected from the list consisting of
1(S),3(R)-Dihydroxy-9,10-secocholesta-5(Z),7(E),10(19),22(E),24-penta-ene (Compound 1),
1(S),3(R)-Dihydroxy-9,10-secocholesta-5(Z),7(E),10(19),22(Z),24-penta-ene (Compound 2),
20(S),1(S),3(R)-Dihydroxy-9,10-secocholesta-5(Z),7(E),10(19),22(E),24-penta-ene (Compound 3),
1(S),3(R)-Dihydroxy-9,10-seco-26,27-cyclo-cholesta-5(Z),7(E),10(19),22(E),24-penta-ene (Compound 4),
20(S),1(S),3(R)-Dihydroxy-9,10-seco-26,27-cyclo-cholesta-5(Z),7(E),10(19),22(E),24-penta-ene (Compound 5),
1(S),3(R)-Dihydroxy-9,10-seco-26,27-methano-cholesta-5(Z),7(E),10(19),22(E),24-penta-ene (Compound 6),
20(S),1(S),3(R)-Dihydroxy-9,10-seco-26,27-methano-cholesta-5(Z),7(E),10(19),22(E),24-penta-ene (Compound 7),
1(S),3(R)-Dihydroxy-20(S)-(4,4-dibromo-1,3-butadien-1yl)-9,10-seco-pregna-5(Z),7(E),10(19)-triene (Compound 8),
1(S),3(S)-Dihydroxy-9,10-secocholesta-5(Z),7(E),10(19) 22(E),24-penta-ene (Compound 23), 1(S),3(R)-Dihydroxxy-26,26,26,27,27,27-hexafluoro-9,
10-secocholesta-5(Z),7(E),10(19), 22(E),24-penta-ene
(Compound 25),
1(S),3(R)-Dihydroxy-20(R)-(4,4-dibromo-1,3-butadien-
1-yl)-9,10-seco-pregna-5(Z),7(E),10(19)-triene (Compound 27),
1(S),3(R)-Dihydroxy-26,27-dimethyl-9,10-secocholesta-
5(Z),7(E),10(19),22(E),24-penta-ene (Compound 28),
1(S),3(S)-Dihydroxy-26,27-dimethyl-9,10-secocholesta-
5(Z),7(E),10(19),22(E),24-penta-ene (Compound 29),
1(S),3(R)-Dihydroxy-24-methyl-26,27-methano-9,10-
secocholesta-5(Z),7(E),10(19),22(E),24-penta-ene
(Compound 30),
1(S),3(R)-Dihydroxy-20(R)-(4,4-dichloro-1,3-butadien-
1-yl)-9,10-seco-pregna-5(Z),7(E),10(19)-triene (Compound 31),
1(S),3(R)-Dihydroxy-26,27-ethano-9,10-secocholesta-5
(Z),7(E),10(19),22(E),24-penta-ene (Compound 32),
1(S),3(R)-Dihydroxy-26,27-propano-9,10-secocholesta-5
(Z),7(E),10(19),22(E),24-penta-ene (Compound 33),
and
20(S),1(S),3(R)-Dihydroxy-26,26,26,27,27,27-
hexafluoro-9,10-secocholesta-5(Z),7(E),10(19), 22(E),
24-penta-ene (Compound 36).

10. A pharmaceutical composition comprising a compound according to claim 1, and optionally a pharmaceutically acceptable carrier.

11. A pharmaceutical composition comprising a compound according to claim 9, and optionally a pharmaceutically acceptable carrier.

\* \* \* \* \*